US009422306B2

(12) United States Patent
Sasaki et al.

(10) Patent No.: US 9,422,306 B2
(45) Date of Patent: Aug. 23, 2016

(54) ARTEMISININ COMPOUNDS AND SYNTHESIS AND USE THEREOF

(71) Applicant: University of Washington Through Its Center for Commercialization, Seattle, WA (US)

(72) Inventors: Tomikazu Sasaki, Seattle, WA (US); Shusheng Wang, Seattle, WA (US)

(73) Assignee: UNIVERSITY OF WASHINGTON THROUGH ITS CENTER FOR COMMERCIALIZATION, Seattle, WA (US)

( * ) Notice: Subject to any disclaimer, the term of this patent is extended or adjusted under 35 U.S.C. 154(b) by 0 days.

(21) Appl. No.: 14/652,263

(22) PCT Filed: Dec. 19, 2013

(86) PCT No.: PCT/US2013/076707
§ 371 (c)(1),
(2) Date: Jun. 15, 2015

(87) PCT Pub. No.: WO2014/100486
PCT Pub. Date: Jun. 26, 2014

(65) Prior Publication Data
US 2015/0344493 A1     Dec. 3, 2015

Related U.S. Application Data

(60) Provisional application No. 61/740,950, filed on Dec. 21, 2012.

(51) Int. Cl.
*C07D 493/18* (2006.01)
*C07D 519/00* (2006.01)

(52) U.S. Cl.
CPC ............ *C07D 493/18* (2013.01); *C07D 519/00* (2013.01)

(58) Field of Classification Search
CPC .......................... C07D 493/18; C07D 519/00
See application file for complete search history.

(56) References Cited

U.S. PATENT DOCUMENTS

2010/0266570 A1   10/2010   Begue et al.
2011/0152289 A1*   6/2011   Begue .................. C07D 519/00
                                                            514/254.11

FOREIGN PATENT DOCUMENTS

WO        03/095444 A1   11/2003
WO     2006/002105 A1    1/2006
WO     2008/046109 A2    4/2008
WO     2010/135427 A2   11/2010

OTHER PUBLICATIONS

Wang, S. et al., "Synthesis of artemisinin dimers using the Ugi reaction and their in vitro efficacy on breast cancer cells", Bioorganic & Medicinal Chemistry Letters, vol. 23, 2013, pp. 4424-4427.

International Search Report mailed on Apr. 8, 2014 for PCT/US2013/76707, filed on Dec. 19, 2013.
Therasse P et al. "New guidelines to evaluate the response to treatment in solid tumors," JNCI 92:205-216, 2000.
Rubin et al. "A small-molecule antagonist of CXCR4 inhibits intracranial growth of primary brain tumors," PNAS 100:13513-13518, 2003.
Connolly DC et al., "Female mice chimeric for expression of the simian virus 40 TAg under control of the MISIIR promoter develop epithelial ovarian cancer," Cancer Res. 63:1389-1397, 2003.
Liu J et al., "A genetically defined model of human ovarian cancer," Cancer Res. 64:1655-1663, 2004.
De Bernardis F et al. "Evidence that members of the secretory aspartyl proteinase gene family, in particular SAP2, are virulence factors for Candida vaginitis," J. Infect. Dis. 179:201-208, 1999.
Armstrong et al., Multiple-component condensation strategies for combinatorial library synthesis. Acc. Chem. Res., 29(3)123-131 (1996).
Bossio et al., Studies on isocyanides and related compounds. Synthesis of benzofuran derivatives. Synthesis, 11:999-1000 (1991).
Buser et al., 7-Oxanorbornane and norbornane mimics of a distorted β-D-mannopyranoside: Synthesis and evaluation as β-mannosidase inhibitors. Helvetica Chimica Acta, 88(12):3151-3173 (2005).
Chadwick et al., Synthesis and biological evaluation of extraordinarily potent C-10 carba artemisinin dimers against *P. falciparum* malaria parasites and HL-60 cancer cells. Bioorganic & Medicinal Chemistry, 17(3):1325-1338 (2009).
Dondorp et al., Artesunate versus quinine in the treatment of severe falciparum malaria in African children (AQUAMAT): an open-label, randomised trial. Lancet, 376(9753):1647-1657 (2010).
Kaim et al., Phenol Ugi—smiles systems: strategies for the multicomponent N-arylation of primary amines with isocyanides, aldehydes, and phenols. Angew. Chem. Int. Ed., 44(48):7961-7964 (2005).
Kunz et al., Asymmetric synthesis on carbohydrate templates: stereoselective Ugi-synthesis of alpha-amino acid derivatives. J. Am. Chem. Soc., 110(2):651-652 (1988).
Kunz et al., Carbohydrates as chiral templates: diastereoselective Ugi synthesis of (S)-amino acids using O-acylated D-arabinopyranosylamine as the auxiliary. Tetrahedron Letters, 30(31):4109-4110 (1989).
Lai et al., Effects of artemisinin-tagged holotransferrin on cancer cells. Life Sciences, 76(11):1267-1279 (2005).
Lockhoff, Dr. Oswald, An access to glycoconjugate libraries through multicomponent reactions. Angew. Chem. Int. Ed., 37(24):3436-3439 (1998).

(Continued)

*Primary Examiner* — Erich A Leeser
(74) *Attorney, Agent, or Firm* — K&L Gates LLP; Louis C. Cullman; Michelle Glasky Bergman

(57) ABSTRACT

The present disclosure describes artemisinin compounds. The compounds can be synthesized using an Ugi synthesis reaction and can be used in the treatment of cancers, parasitic infections and yeast infections.

23 Claims, 7 Drawing Sheets

(56) References Cited

OTHER PUBLICATIONS

Maude et al., Does artesunate prolong the electrocardiograph QT interval in patients with severe malaria? Am. J. Trop. Med. Hyg., 80(1):126-132 (2009).

Mori et al., Synthesis of mono- and sesquiterpenoids, XVI: Synthesis of (−)-pereniporins A and B, sesquiterpene antibiotics from a basidiomycete. Liebigs Ann. Chem., (9):939-943 (1989).

Morrissey et al., Effect of artemisinin derivatives on apoptosis and cell cycle in prostate cancer cells. Anti-cancer Drugs, 21(4):423-432 (2010).

Nakamura et al., A two-step, one-pot synthesis of diverse N-pyruvoyl amino acid derivatives using the Ugi reaction. Bioorganic & Medicinal Chemistry Letters, 10(24):2807-2810 (2000).

Nam et al., Effects of artemisinin and its derivatives on growth inhibition and apoptosis of oral cancer cells. Head & Neck, 29(4):335-340 (2007).

Paik et al., Second generation, orally active, antimalarial, artemisinin-derived trioxane dimers with high stability, efficacy, and anticancer activity. J. Med. Chem., 49(9):2731-2734 (2006).

Posner et al., Orally active, antimalarial, anticancer, artemisinin-derived trioxane dimers with high stability and efficacy. J. Med. Chem., 46(6):1060-1065 (2003).

Rosenthal et al., Malaria-infected mice are cured by a single oral dose of new dimeric trioxane sulfones which are also selectively and powerfully cytotoxic to cancer cells. J. Med. Chem., 52(4):1198-1203 (2009).

Ross et al., Stereoselective U-4CRs with 1-amino-5-desoxy-5-thio-2,3,4-O-isobutanoyl-β-D-xylopyranose—an effective and selectively removable chiral auxiliary. Tetrahedron, 58(30):6127-6133 (2002).

Sigmüller et al., Chiral perrocenylalkylamines from (−)-menthone. Tetrahedron, 42(21):5931-5940 (1986).

Stockwin et al., Artemisinin dimer anticancer activity correlates with heme-catalyzed reactive oxygen species generation and endoplasmic reticulum stress induction. Int. J. Cancer, 125(6):1266-1275 (2009).

Taylor et al., Antimalarial drug toxicity, a review. Drug Safety, 27(1):25-61 (2004).

Ugi et al., Ugi reactions with trifunctional α-amino acids, aldehydes, isocyanides and alcohols. Tetrahedron, 52 (35):11657-11664 (1996).

White, N.J., Qinghaosu (artemisinin): The price of success. Science, 320(5874):330-334 (2008).

Oh et al., Synthesis and anti-cancer activity of covalent conjugates of artemisinin and a transferrin-receptor targeting peptide. Cancer Letters, 274(1):33-39 (2009).

* cited by examiner

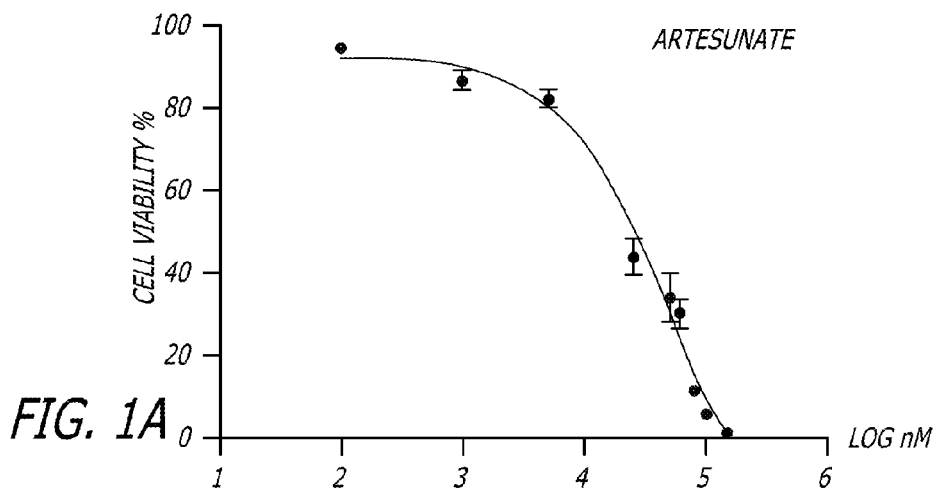
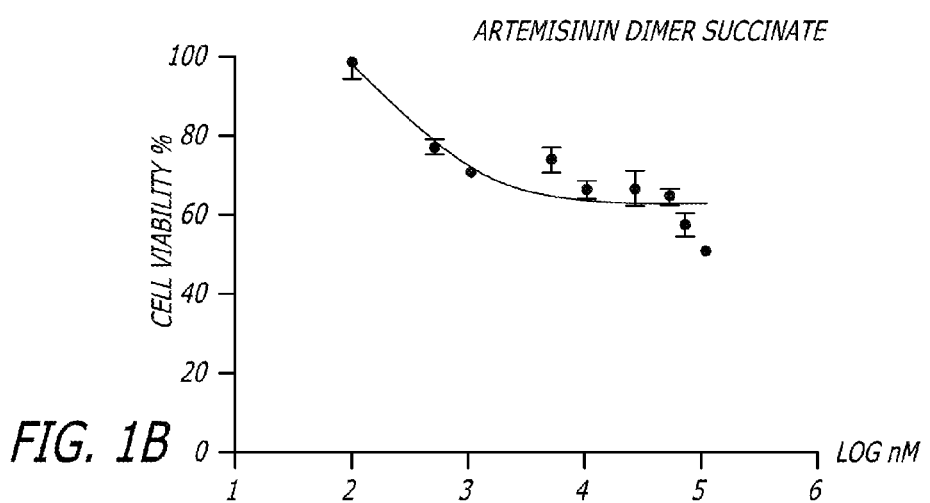
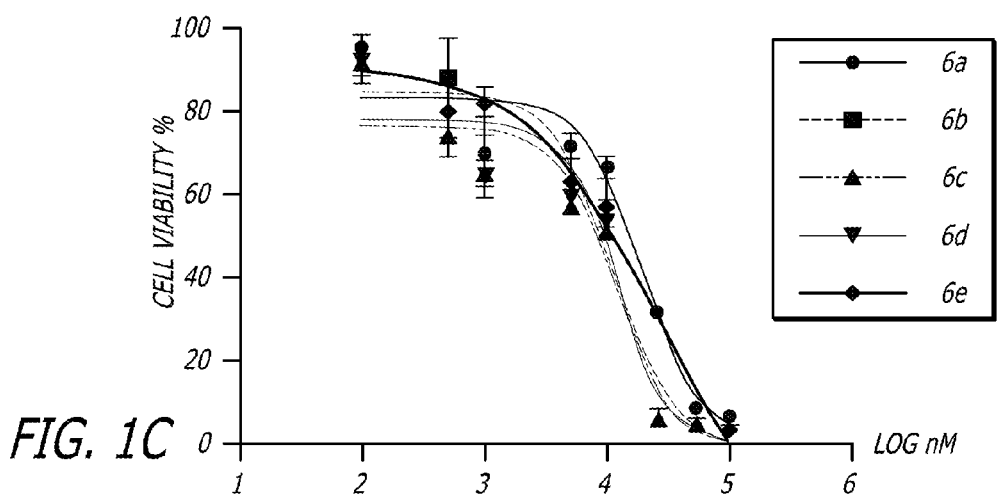

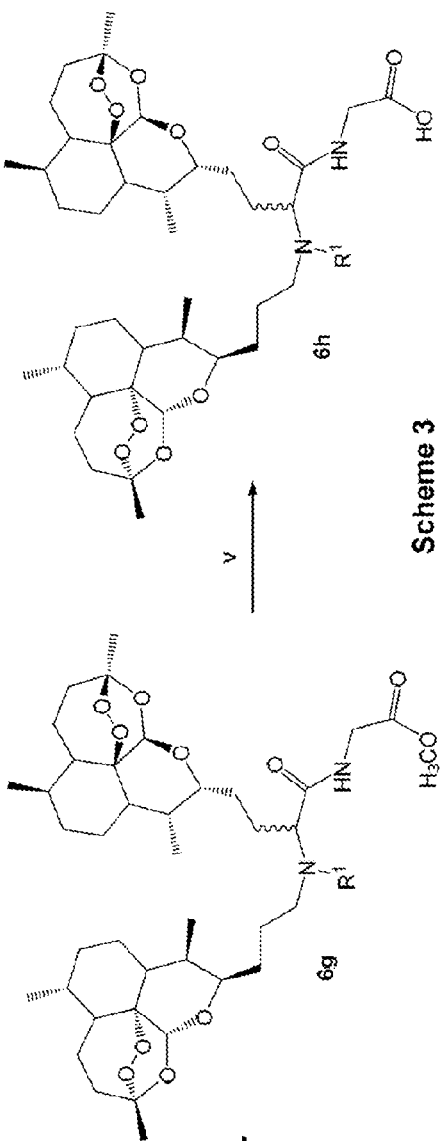
FIG. 5
Scheme 3
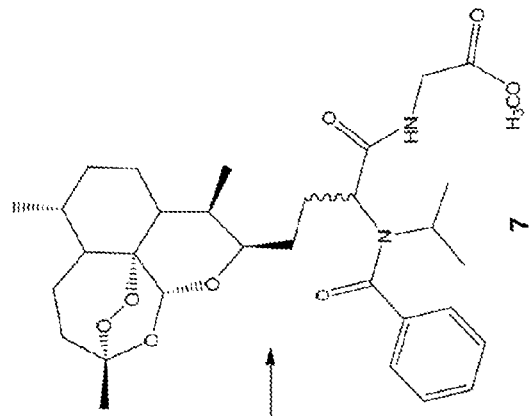
FIG. 6
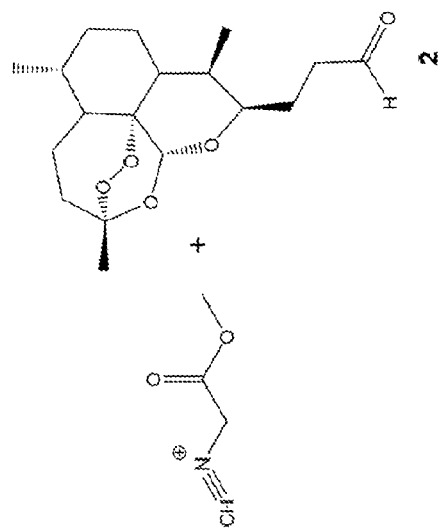
Scheme 4

ARTEMISININ COMPOUNDS AND SYNTHESIS AND USE THEREOF

CROSS REFERENCE TO RELATED APPLICATION

This application is a national phase of PCT/US2013/076707 filed on Dec. 19, 2013 which claims the benefit of U.S. Provisional Application No. 61/740,950, filed Dec. 21, 2012, the entire disclosures of both of which are herein incorporated by reference.

FIELD OF THE DISCLOSURE

The present disclosure describes artemisinin monomers and dimers, and methods of synthesis and use thereof. Methods of synthesis include use of the Ugi reaction and methods of use include treating cancers, parasitic infections and yeast infections.

BACKGROUND OF THE DISCLOSURE

Artemisinin is a naturally occurring peroxide isolated from the Chinese medicinal plant, *Artemisia annua* L. Artemisinin and its derivatives have been used as therapeutic compounds and have excellent safety profiles. For example, naturally occurring artemisinin has been shown to have anti-malarial and anti-cancer properties.

SUMMARY OF THE DISCLOSURE

The present disclosure describes new artemisinin monomers and dimers (collectively referred to as "compounds") that can be created synthetically using an Ugi reaction. The compounds can be used to treat cancers, parasitic infections and yeast infections.

In particular embodiments, the dimers can have a chemical structure of:

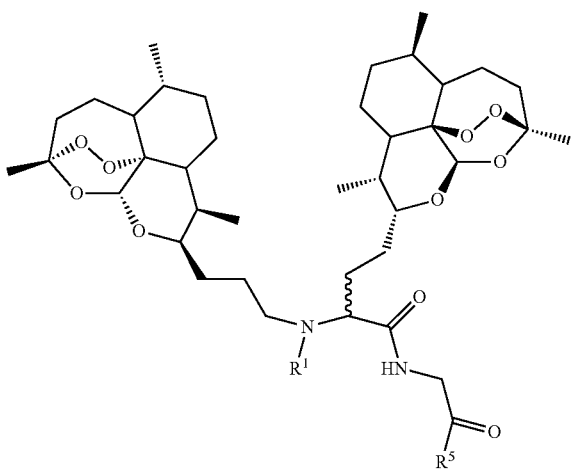

wherein $R^1$ and $R^5$ are as defined herein.

In particular embodiments, the monomers can have a chemical structure of:

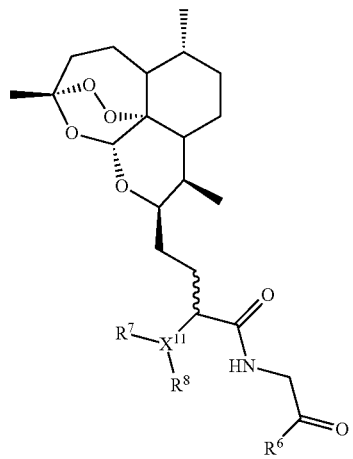

wherein $X^{11}$, $R^6$, $R^7$, and $R^8$ are as defined herein.

BRIEF DESCRIPTION OF THE DRAWINGS

FIG. 5 illustrates synthesis Scheme 3.

FIG. 6 illustrates synthesis Scheme 4.

DETAILED DESCRIPTION

Figure 1D:
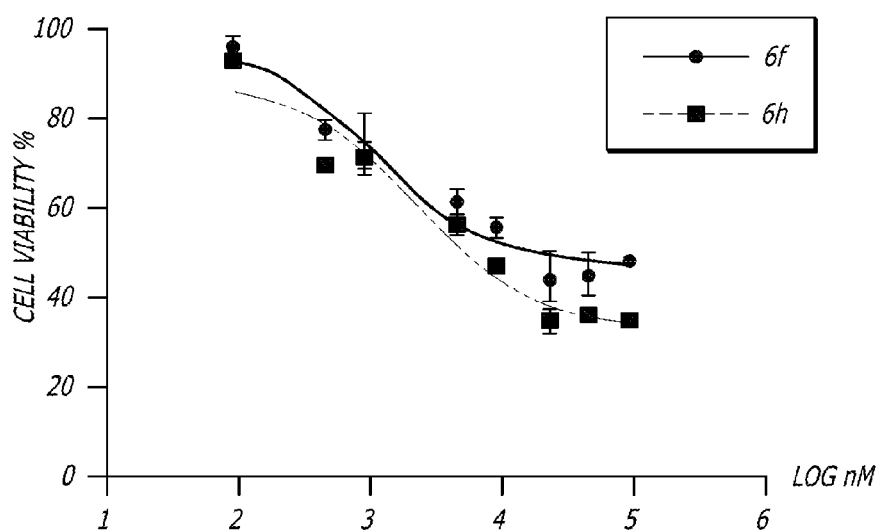
FIG. 1 illustrates effects of (A) artesunate, (B) artemisinin dimer succinate, (C) artemisinin dimer 6a-6e, (D) artemisinin dimer 6f and 6h, and (E) artemisinin monomer 7 on an MDA MB 231 cell line.
Figure 1E:
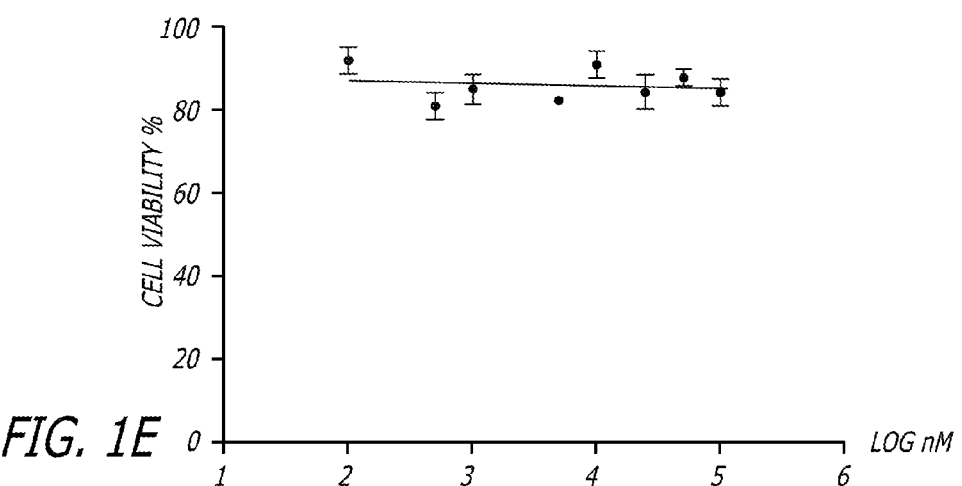
Figure 2A:
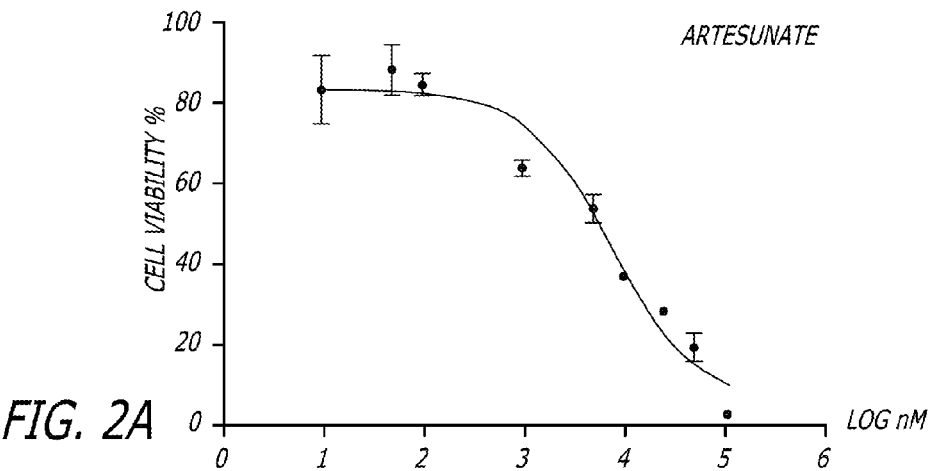
FIG. 2(A)-(E) illustrate effects of the same compounds as described in relation to FIG. 1A on a BT474 cell line.
Figure 2B:
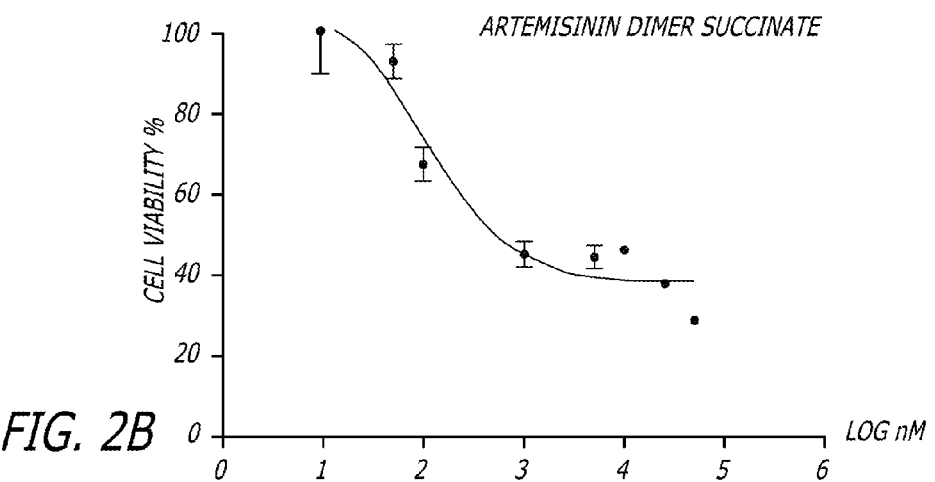
Figure 2C:
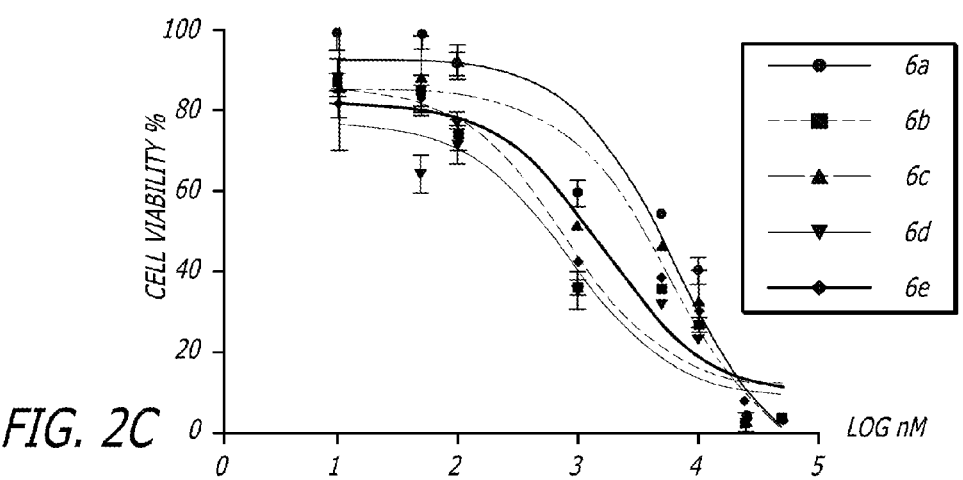
Figure 2D:
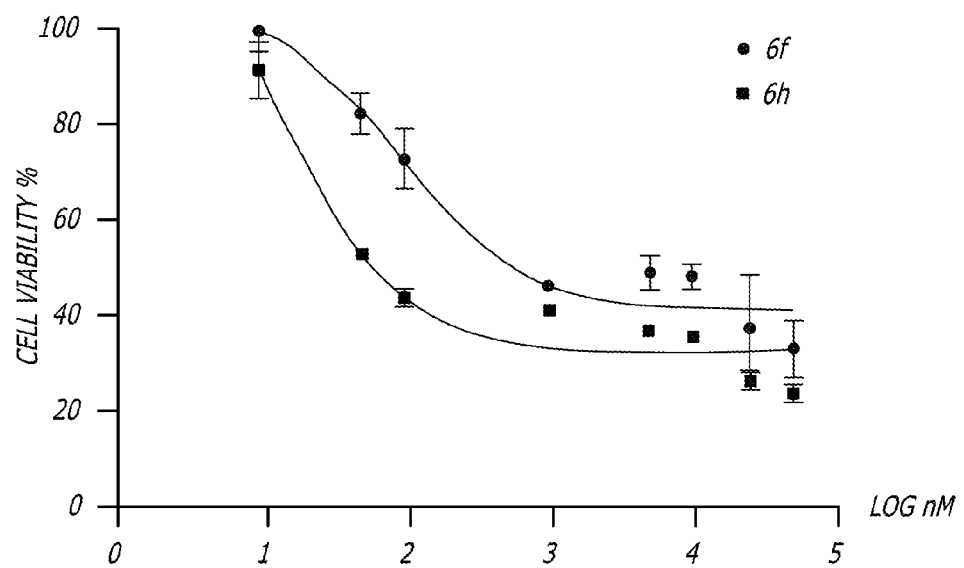
Figure 2E:
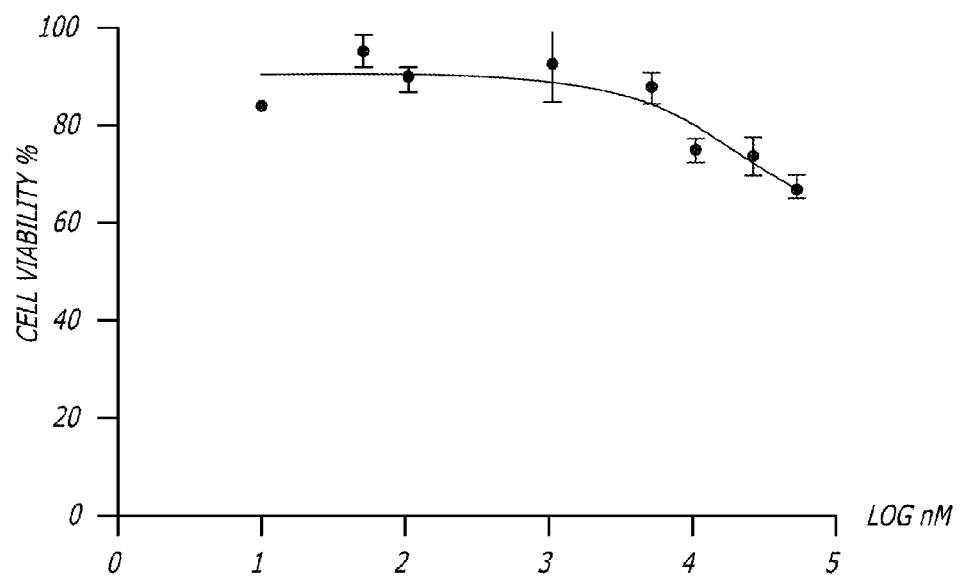

Artemisinin is a naturally occurring peroxide isolated from the Chinese medicinal plant, *Artemisia annua* L. Artemisinin and its derivatives have been used as therapeutic compounds and have excellent safety profiles. For example, naturally occurring artemisinin has been shown to have anti-cancer and anti-malarial properties.

The present disclosure describes new artemisinin monomers and dimers (collectively referred to as "compounds") that can be created synthetically using an Ugi reaction. The compounds can be used to treat cancers, parasitic infections and yeast infections.

I. Structure of Compounds

An artemisinin dimer disclosed herein can have a structure of:

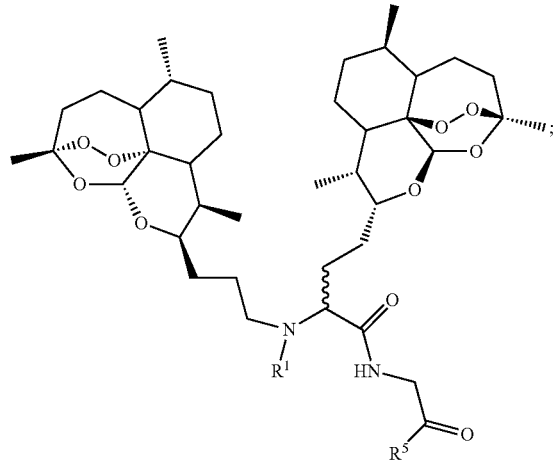

wherein $R^1$ is

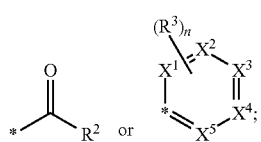

$R^2$ is H, $CH_3$, $CCl_3$, $CBr_3$, $OF_3$, OH, $NH_2$, or

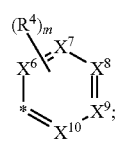

$R^3$ and $R^4$ are each independently H, Cl, Br, I, F, $CH_3$, $CCl_3$, $CBr_3$, $CF_3$, a $C_1$-$C_6$ alkyl substituted with one or more Cl, Br, OH, or F, $NO_2$, $CH_2OH$, $CH_2CH_2OH$, $OCH_3$, $OCH_2CH_3$, $CO_2H$, $NH_2$, $N(CH_3)_2$, $N(CCl_3)_2$, $N(CBr_3)_2$, or $N(CF_3)_2$;

$R^5$ is H, OH, $OCH_3$, or $OCH_2CH_3$;

n is 0, 1, 2, 3, 4, or 5;

m is 0, 1, 2, 3, 4, or 5; and $X^1$, $X^2$, $X^3$, $X^4$, $X^5$, $X^6$, $X^7$, $X^8$, $X^9$, and $X^{10}$ are each independently CH, N, O or S.

In some embodiments, $X^1$, $X^2$, $X^3$, $X^4$, $X^5$, $X^6$, $X^7$, $X^8$, $X^9$, and $X^{10}$ are each independently CH or N. In other embodiments, $X^1$, $X^2$, $X^3$, $X^4$, $X^5$, $X^6$, $X^7$, $X^8$, $X^9$, and $X^{10}$ are each CH.

In other embodiments, $R^1$ is

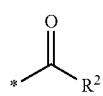

wherein $R^2$ is $CF_3$.

In further embodiments, $R^3$ is $NH_2$ or $OCH_3$. In one embodiment, n is 1 and $R^4$ is $NO_2$ or n is 4 and $R^4$ is F.

In still other embodiments, $R^1$ is

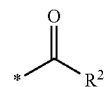

and $R^2$ is

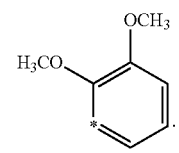

In some embodiments, $R^5$ is OH, $OCH_3$, or a ketone group such as a $C_1$-$C_6$ alkyl ketone.

In one example embodiment, referred to herein as "6a", the compound can have a structure of:

6a

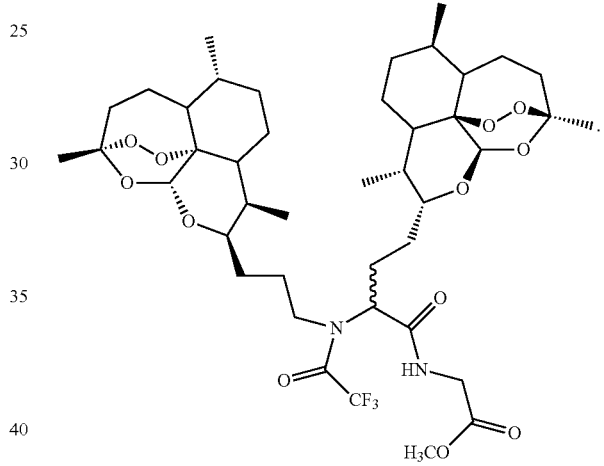

In another example embodiment, referred to herein as "6b", the compound can have a structure of:

6b

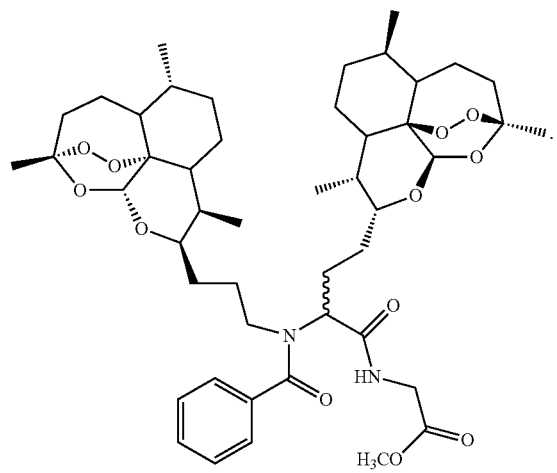

In another example embodiment, referred to herein as "6c", the compound can have a structure of:

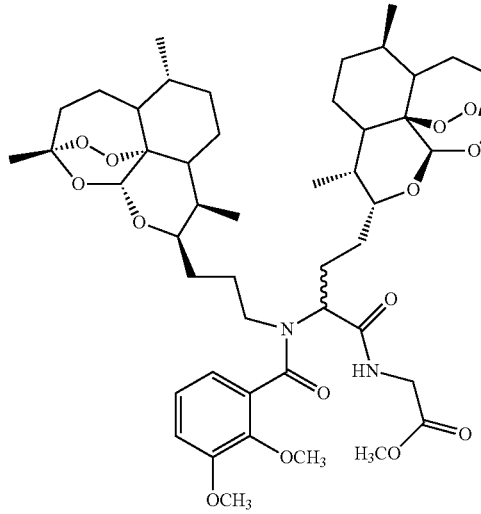

6c

In another example embodiment, referred to herein as "6d", the compound can have a structure of:

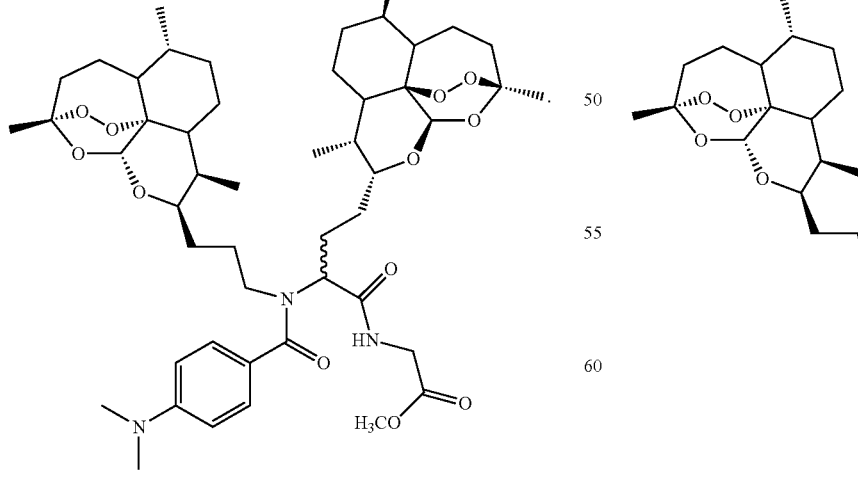

6d

In another example embodiment, referred to herein as "6e", the compound can have a structure of:

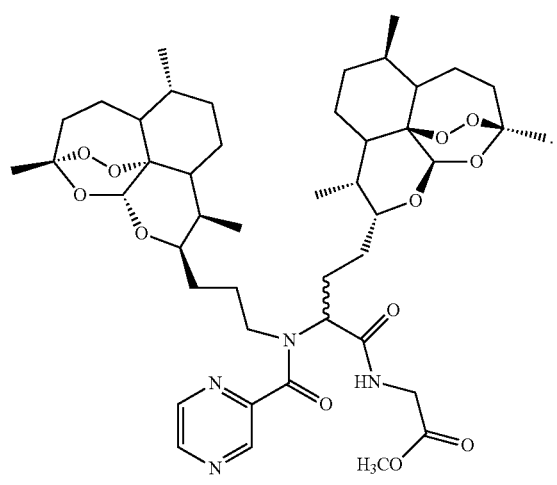

6e

In another example embodiment, referred to herein as "6f", the compound can have a structure of:

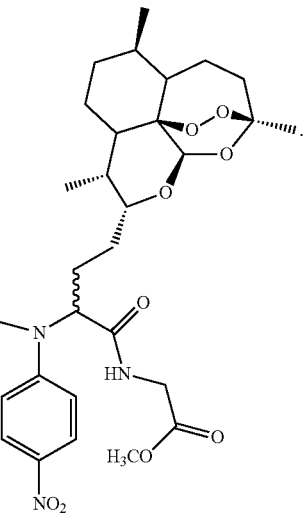

6f

In another example embodiment, referred to herein as "6g", the compound can have a structure of:

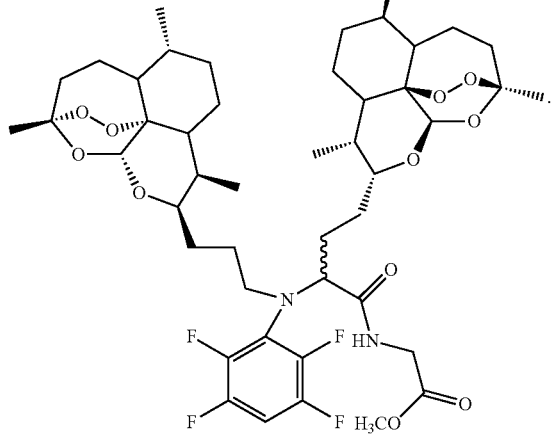

6g

In another example embodiment, compounds described herein can have a structure of:

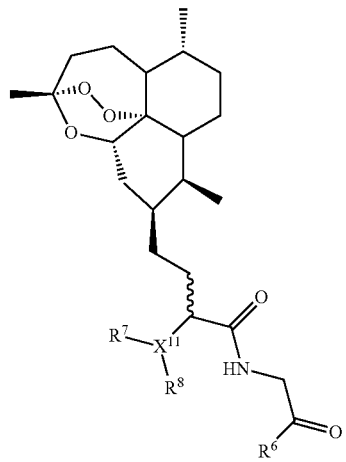

wherein R$^6$ is H, Cl, Br, I, F, CH$_3$, CCl$_3$, CBr$_3$, CF$_3$, a C$_1$-C$_6$ alkyl substituted with one or more Cl, Br, OH, or F, NO$_2$, OH, CH$_3$OH, CH$_3$CH$_2$OH, OCH$_3$, OCH$_2$CH$_3$, CO$_2$, NH$_2$, N(CH$_3$)$_2$, N(CCl$_3$)$_2$, N(CBr$_3$)$_2$, or N(CF$_3$)$_2$;

R$^7$ is H, Cl, Br, I, F, CH$_3$, CCl$_3$, CBr$_3$, CF$_3$, a C$_1$-C$_6$ alkyl substituted with one or more Cl, Br, OH, or F, CH(CH$_3$)$_2$, NO$_2$, CH$_2$OH, CH$_2$CH$_2$OH, OCH$_3$, OCH$_2$CH$_3$, CO$_2$H, NH$_2$, N(CH$_3$)$_2$, N(CCl$_3$)$_2$, N(CBr$_3$)$_2$, or N(CF$_3$)$_2$;

R$^8$ is

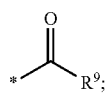

R$^9$ is H, CH$_3$, CCl$_3$, CBr$_3$, CF$_3$, OH, NH$_2$, or

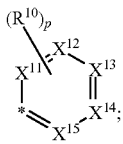

R$^{10}$ is H, Cl, Br, I, F, CH$_3$, CCl$_3$, CBr$_3$, CF$_3$, a C$_1$-C$_6$ alkyl substituted with one or more Cl, Br, OH, or F, NO$_2$, CH$_2$OH, CH$_2$CH$_2$OH, OCH$_3$, OCH$_2$CH$_3$, CO$_2$H, NH$_2$, N(CH$_3$)$_2$, N(CCl$_3$)$_2$, N(CBr$_3$)$_2$, or N(CF$_3$)$_2$;

p is 0, 1, 2, 3, 4, or 5; and

X$^{11}$, X$^{12}$, X$^{13}$, X$^{14}$, and X$^{15}$ are each independently CH, N, O or S.

In some embodiments, X$^{11}$, X$^{12}$, X$^{13}$, X$^{14}$, and X$^{15}$ can each independently be CH or N. In one embodiment, X$^{11}$, X$^{12}$, X$^{13}$, X$^{14}$, and X$^{15}$ are each CH.

In other embodiments, R$^9$ is

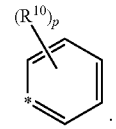

In one embodiment, R$^9$ is benzene and/or p is 0. In still other embodiments, R$^7$ is CH(CH$_3$)$_2$.

In one example embodiment, the compound can have a structure

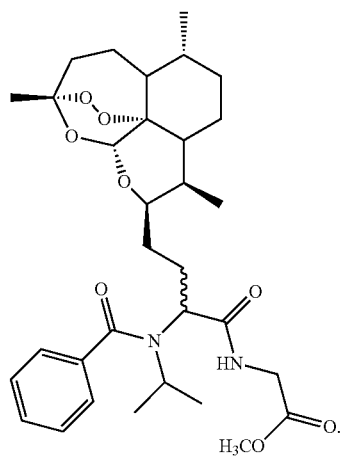

II. Synthesis of Compounds

Figure 3:
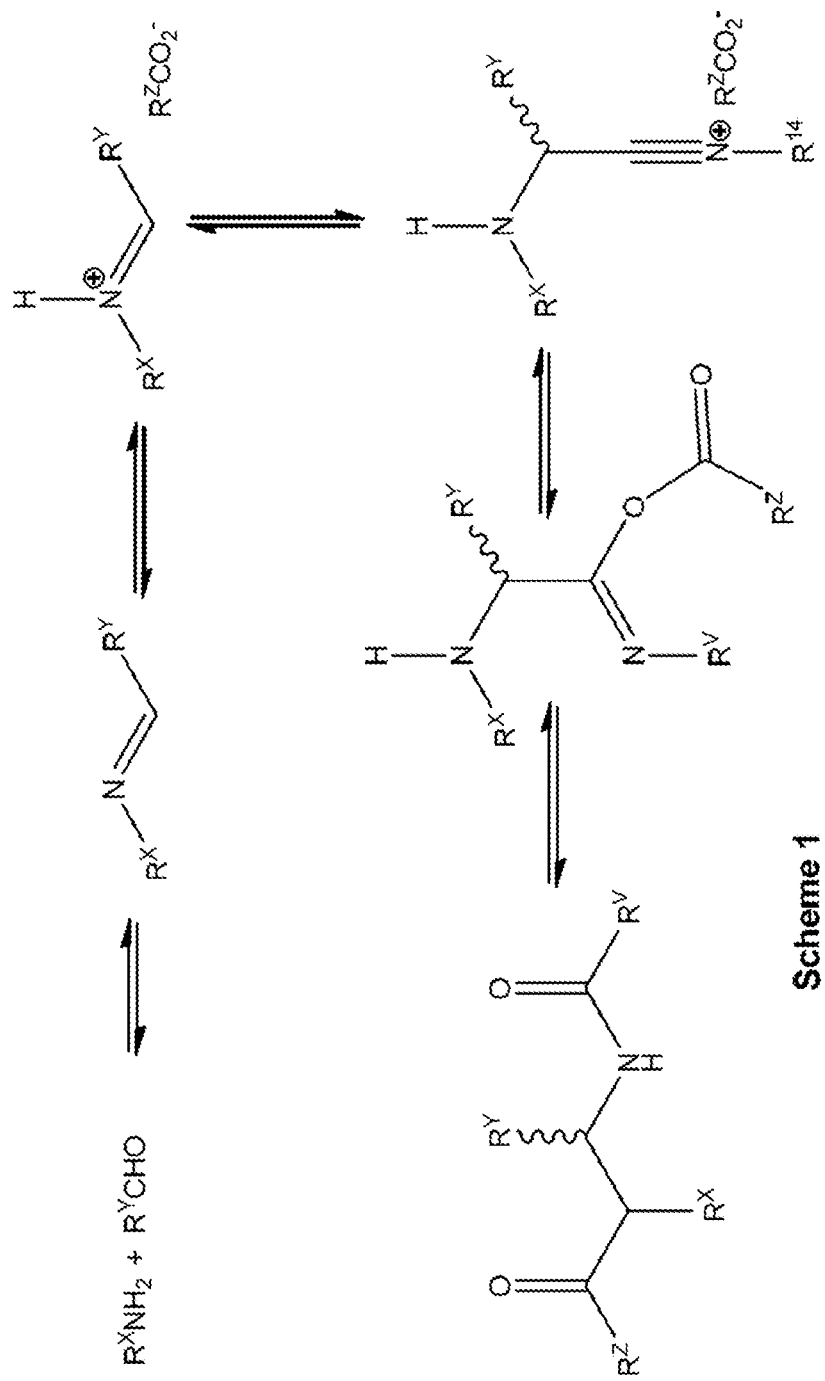
FIG. 3 illustrates synthesis Scheme 1.

Methods of making the compounds disclosed herein can include use of an Ugi reaction. In the Ugi reaction (FIG. 3; Scheme 1), the initially formed imine reacts with isocyanide and carboxylic acid to form an intermediate that undergoes rearrangement to give the final dipeptide product.

Figure 4:
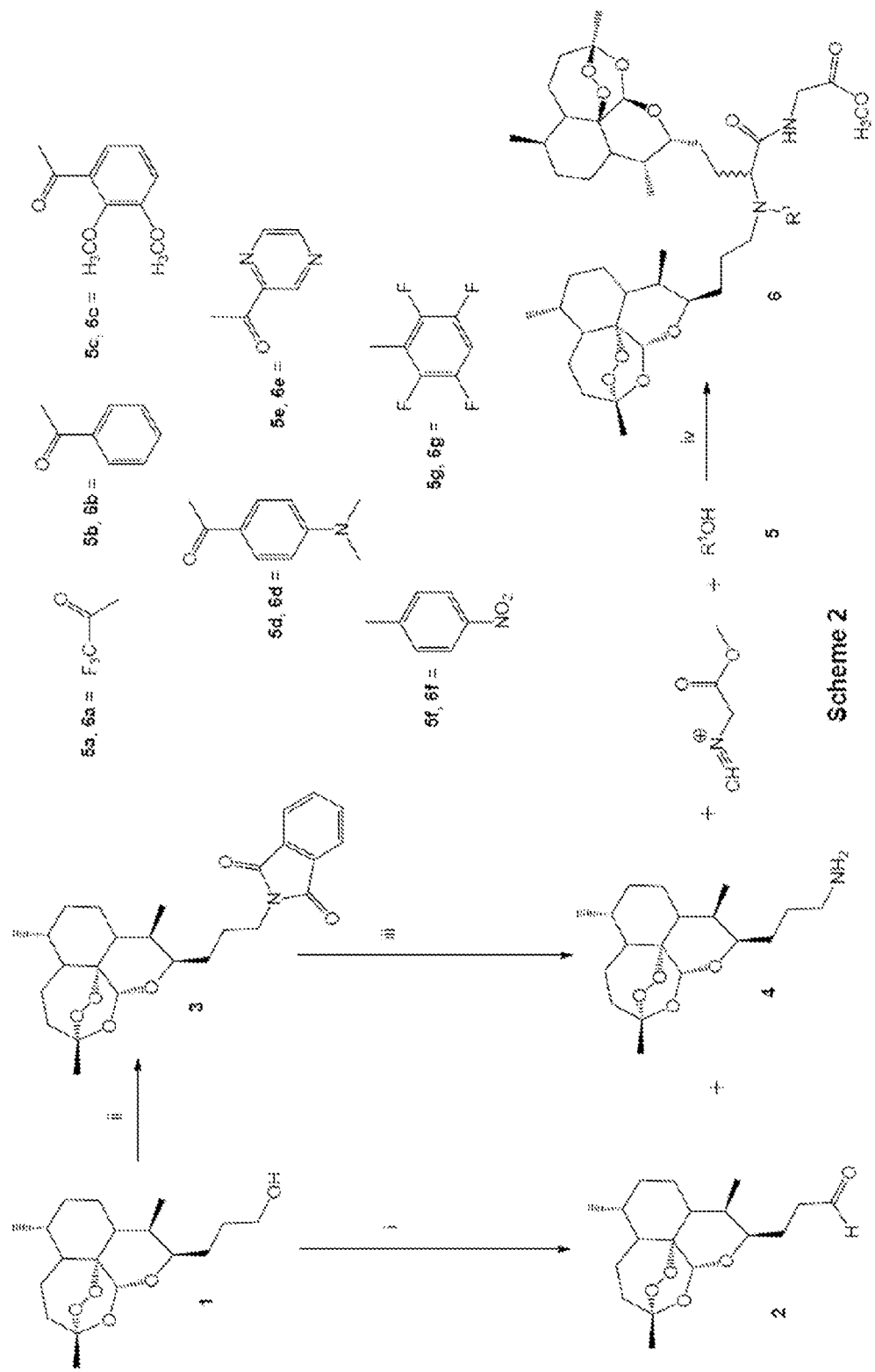
FIG. 4 illustrates synthesis Scheme 2.

To utilize an Ugi reaction to form the compounds described herein, different artemisinin monomers can be prepared as building blocks. Preparation of two exemplary artemisinin monomers are described in FIG. 4; Scheme 2.

The reagents and conditions used in Scheme 2 can be as follows: (i) benzene, dimethyl sulfoxide, pyridine, trifluoroacetic acid, N,N-dicyclohexylcarbodiimide, room temperature for 18 hr; (ii) triphenyl phosphine (Ph$_3$P), phthalimide, diisopropyl azodicarboxylate (DIAD), tetrahydrofuran (THF), 50° C. for 4 hr; (iii) NH$_2$NH$_2$H$_2$O, ethanol, at 50° C. overnight; and (iv) methanol, room temperature, overnight.

A Moffatt oxidation of artemisinin primary alcohol (1) furnished artemisinin aldehyde (2). The Moffatt oxidation reaction can result in a 91% chemical yield. Artemisinin amine (4) another component of an Ugi reaction, was prepared by a Mistunobu reaction. The Artemisinin primary alcohol (1) was first converted to artemisinin phthalimide (3). The reaction can result in a 90% chemical yield using PPh$_3$ and DIAD, followed by hydrazinolysis in ethanol at 50° C., to give artemisinin amine (4). This reaction can result in a 75% chemical yield.

Two other components for the Ugi reaction include a carboxylic acid and an isonitrile. For the carboxylic acid component, carboxylic acids (5a-5e) can be included. Phenols with strong electrical withdrawing groups can also be used as acid components in the Ugi reaction, due to their significant acidity.

In addition to carboxylic acids, p-nirophenol (5f) and 2,3,5,6-tetrafluorophenol (5g) can be used to synthesize artemisinin dimers. A series of artemisinin dimers can be synthesized by combining all four components in Ugi reaction conditions: after stirring artemisinin aldehyde (2) artemisinin amine (4) and an acid component (5a-5g) respectively, in anhydrous methanol at room temperate for 30 min, methyl isocyanoacetate can be added. In some embodiments, the reaction can be run overnight at room temperature.

Using the conditions described above, after chromatographic purification, at least six artemisinin dimers (6a-6f) can be obtained. A chemical yield of 20%-90% or 22%-68% can be achieved. For example, Compound 6a can be attained at a yield of 60%, 68% or greater. Compound 6b can be attained at a yield of 50%, 52% or greater. Compound 6c can be attained at a yield of 30%, 33% or greater. Compound 6d can be attained at a yield of 20%, 22% or greater. Compound 6e can be attained at a yield of 50%, 55% or greater. Compound 6f can be attained at a yield of 30%, 33% or greater. Compound 6h can be attained at a yield of 30%, 33% or greater. Compound 7 can be attained at a yield of 30%, 38% or greater.

The ratio of diastereomeric products can be determined by $^1$H NMR. Following particular reactions, these ratios were found to be: 6a=1:0.88; 6b=1:0.79; 6c=1:0.5; 6d=1:1.1; 6e=1:0.83; 6f=1:0.6; 6g=1:0.93.

NMR and MS (MALDI-MS) indicated that artemisinin dimer 6g may undergo hydrolysis of methyl ester during synthesis. Without being bound by theory, this may be a result of a trans-esterification reaction with phenol. Thus, the carboxylic acid (6h), instead of (6g) can be reacted as under FIG. 5; Scheme 3. Scheme 3 utilizes methanol at room temperature overnight.

In addition to artemisinin dimers, artemisinin monomer 7 was also prepared. Monomer (7) was synthesized using an Ugi synthesis procedure as illustrated in FIG. 6; Scheme 4. Scheme 4 can utilize methanol at room temperature overnight. The ratio of diastereomeric products was 1:0.55.

The reaction schemes described herein show that the Ugi reaction is compatible with peroxide compounds such as artemisinin. Chiral artemisinin monomers may affect stereochemical outcomes of the Ugi reaction. $^1$H-NMR studies, for example, illustrate that compounds 6c and 7 showed the highest diastereomeric excess of 33%, and other compounds showed less than 25% diastereomeric excesses. Stereoselectivities of the described artemisinin dimer synthesis can be improved by bringing the reactive amino group closer to the artemisinin core.

III. Use of Compounds

The compounds described can be used to treat a condition or a disease in a subject. Exemplary subjects include mammals, reptiles, amphibians, birds, or fish. Exemplary subjects also include humans, veterinary animals, livestock and research animals. Veterinary animals include, without limitation, dogs, cats and horses. Livestock includes, without limitation, cattle, llama, sheep, buffalo, chickens and goats. Research animals include, without limitation, monkeys, rats, mice, fish, flies and worms.

Treating a subject includes delivering an effective amount or delivering a prophylactic treatment and/or a therapeutic treatment. An "effective amount" is the amount of a compound necessary to result in a desired physiological change in the subject. Effective amounts are often administered for research purposes.

A "prophylactic treatment" includes a treatment administered to a subject who does not display signs or symptoms of a disease or condition or displays only early signs or symptoms of a disease or condition such that treatment is administered for the purpose of diminishing, preventing, or decreasing the risk of developing the disease or condition further. Thus, a prophylactic treatment functions as a preventative treatment against a disease or disorder.

A "therapeutic treatment" includes a treatment administered to a subject who displays symptoms or signs of a disease or condition and is administered to the subject for the purpose of diminishing or eliminating those signs or symptoms of the disease or condition.

"Therapeutically effective amounts" include those that provide prophylactic treatment and/or therapeutic treatment. Therapeutically effective amounts need not fully prevent or cure the disease or condition but can also provide a partial benefit, such as delay of onset or alleviation or improvement of at least one symptom of the disease or condition.

For administration, effective amounts and therapeutically effective amounts (also referred to herein as doses) can be initially estimated based on results from in vitro assays and/or animal model studies. For example, a dose can be formulated in animal models to achieve a circulating concentration range that includes the IC$_{50}$ as determined in cell culture. Such information can be used to more accurately determine useful doses in subjects of interest.

The actual dose amount administered to a particular subject can be determined by a physician, veterinarian or researcher taking into account parameters such as physical and physiological factors including body weight, severity of condition, type of disease, previous or concurrent therapeutic interventions, idiopathy of the subject and route of administration.

Useful doses often range from 0.1 to 5 mg/kg/day or from 0.5 to 1 mg/kg/day or from 0.1 to 5 µg/kg/day or from 0.5 to 1 µg/kg/day. In other non-limiting examples, a dose can comprise 1 µg/kg/day, 5 µg/kg/day, 10 µg/kg/day, 50 µg/kg/day, 100 µg/kg/day, 200 µg/kg/day, 350 µg/kg/day, 500 µg/kg/day, 1 mg/kg/day, 5 mg/kg/day, 10 mg/kg/day, 50 mg/kg/day, 100 mg/kg/day, 200 mg/kg/day, 350 mg/kg/day, 500 mg/kg/day or 1000 mg/kg/day. Therapeutically effective amounts can be achieved by administering single or multiple doses during the course of a treatment regimen (days, weeks, months, etc.).

In some embodiments, at least one compound is provided as part of a pharmaceutical composition. The pharmaceutical composition can comprise, for example, at least 0.1% w/v of a compound. In other embodiments, the pharmaceutical composition can comprise between 2% to 75% of compound per weight of the pharmaceutical composition, or between 25% to 60% of compound per weight of the pharmaceutical composition.

In one embodiment, a pharmaceutical composition includes at least compound 7, at least compound 6a, at least compound 6b, at least compound 6c, at least compound 6d, at least compound 6e, at least compound 6f or at least compound 6g. Combinations of various compounds can also be beneficially employed. For example, one embodiment of a pharmaceutical composition includes compounds 6a, 6f and 6e. Another embodiment includes compounds 7, 6b and 6f. Another embodiment includes compounds 6c and 6g. Another embodiment includes compounds 6a and 6c. Any possible combination of compounds disclosed herein can be provided a part of a pharmaceutical composition.

Pharmaceutically acceptable salts, tautomers and isomers of the compounds disclosed herein can also be used. Exemplary salts include sulfate, citrate, acetate, oxalate, chloride, bromide, iodide, nitrate, bisulfate, phosphate, acid phosphate, isonicotinate, lactate, salicylate, acid citrate, tartrate, oleate, tannate, pantothenate, bitartrate, ascorbate, succinate, maleate, besylate, gentisinate, fumarate, gluconate, glucaronate, saccharate, formate, benzoate, glutamate, methanesulfonate, ethanesulfonate, benzenesulfonate, p-toluenesulfonate, and pamoate (i.e., 1,1'-methylene-bis-(2-hydroxy-3-naphthoate)) salts.

In particular embodiments, the compounds can be conjugated to or with metal containing molecules or complexes. Exemplary metals include transition metals such as Fe, Co, Al, Rh, Ni, Cu, Zn, Mn, Cr, and Rh. In one embodiment, the compounds can be conjugated to an iron-carrying molecule. Exemplary iron-carrying molecules include transferrin, lactoferrin, iron chelators and iron nanoparticles.

The compounds can also be provided as pro-drugs. The term "prodrug" refers to a therapeutic compound that can undergo biotransformation (e.g., either spontaneous or enzymatic) within the subject to release, or to convert (e.g., enzymatically, mechanically, electromagnetically, etc.) an active or more active form of the therapeutic after administration. Prodrugs can be used to overcome issues associated with stability, toxicity, lack of specificity, or limited bioavailability and often offer advantages related to solubility, tissue compatibility, and/or delayed release (See e.g., Bundgard, Design of Prodrugs, pp. 7-9, 21-24, Elsevier, Amsterdam (1985); and Silverman, The Organic Chemistry of Drug Design and Drag Action, pp. 352-401, Academic Press, San Diego, Calif. (1992) both incorporated by reference for their teachings regarding the same).

The formulations described herein can be administered by, without limitation, injection, inhalation, infusion, perfusion, lavage or ingestion. Routes of administration can include intravenous, intradermal, intraarterial, intraperitoneal, intralesional, intracranial, intraarticular, intraprostatic, intrapleural, intratracheal, intranasal, intravitreal, intravaginal, intrarectal, topically, intratumoral, intramuscular, intravesicular, intrapericardial, intraumbilical, intraoculareal, mucosal, oral, subcutaneous and/or subconjunctival.

For injection, formulations can be made as aqueous solutions, such as in buffers such as Hanks' solution, Ringer's solution, or physiological saline. The solutions can contain formulatory agents such as suspending, stabilizing and/or dispersing agents. Alternatively, the formulation can be in lyophilized and/or powder form for constitution with a suitable vehicle, e.g., sterile pyrogen-free water, before use.

For oral administration, the formulations can be made as tablets, pills, dragees, capsules, liquids, gels, syrups, slurries, suspensions and the like. For oral solid formulations such as, for example, powders, capsules and tablets, suitable excipients include binders (gum tragacanth, acacia, cornstarch, gelatin), fillers such as sugars, e.g. lactose, sucrose, mannitol and sorbitol; dicalcium phosphate, starch, magnesium stearate, sodium saccharine, cellulose, magnesium carbonate; cellulose preparations such as maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP); granulating agents; and binding agents. If desired, disintegrating agents can be added, such as corn starch, potato starch, alginic acid, cross-linked polyvinylpyrrolidone, agar, or alginic acid or a salt thereof such as sodium alginate. If desired, solid dosage forms can be sugar-coated or enteric-coated using standard techniques. Flavoring agents, such as peppermint, oil of wintergreen, cherry flavoring, orange flavoring, etc. can also be used.

For administration by inhalation, formulations can be made as aerosol sprays from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of gelatin for use in an inhaler or insufflator may be formulated containing a powder mix of the therapeutic and a suitable powder base such as lactose or starch.

For administration to livestock, the compounds can be advantageously administered in forms suitable for oral administration to livestock such as through drinking water or mixed with feed. Spray-dried formulations are particularly appropriate for addition to livestock feed. Spray-dried compositions can be mixed with any suitable feed, by any method well known to one of ordinary skill in the art. In particular embodiments, spray-dried compositions are provided in an amount of 0.1-1 kg of spray-dried powder per ton of livestock feed. Feed for chicken incorporating compounds disclosed herein can also be formulated in pellets.

Any formulation disclosed herein can advantageously include any other pharmaceutically acceptable carriers which include those that do not produce significantly adverse, allergic or other untoward reactions that outweigh the benefit of administration, whether for research, prophylactic and/or therapeutic treatments. Exemplary pharmaceutically acceptable carriers and formulations are disclosed in Remington's Pharmaceutical Sciences, 18th Ed. Mack Printing Company, 1990, which is incorporated by reference herein for its teachings regarding the same. Moreover, formulations can be prepared to meet sterility, pyrogenicity, general safety and purity standards as required by United States FDA Office of Biological Standards and/or other relevant foreign regulatory agencies.

Exemplary generally used pharmaceutically acceptable carriers include any and all bulking agents or fillers, solvents or co-solvents, dispersion media, coatings, surfactants, antioxidants (e.g., ascorbic acid, methionine, vitamin E), preservatives, isotonic agents, absorption delaying agents, salts, stabilizers, buffering agents, chelating agents (e.g., EDTA), gels, binders, disintegration agents, and/or lubricants.

Exemplary buffering agents include citrate buffers, succinate buffers, tartrate buffers, fumarate buffers, gluconate buffers, oxalate buffers, lactate buffers, acetate buffers, phosphate buffers, histidine buffers and/or trimethylamine salts.

Exemplary preservatives include phenol, benzyl alcohol, meta-cresol, methyl paraben, propyl paraben, octadecyldimethylbenzyl ammonium chloride, benzalkonium halides, hexamethonium chloride, alkyl parabens such as methyl or propyl paraben, catechol, resorcinol, cyclohexanol and 3-pentanol.

Exemplary isotonic agents include polyhydric sugar alcohols including trihydric or higher sugar alcohols, such as glycerin, erythritol, arabitol, xylitol, sorbitol or mannitol.

Exemplary stabilizers include organic sugars, polyhydric sugar alcohols, polyethylene glycol; sulfur-containing reducing agents, amino acids, low molecular weight polypeptides, proteins, immunoglobulins, hydrophilic polymers or polysaccharides.

Formulations can also be depot preparations. Such long acting formulations may be administered by, without limitation, implantation (for example subcutaneously or intramuscularly) or by intramuscular injection. Thus, for example, compounds can be formulated with suitable polymeric or hydrophobic materials (for example as an emulsion in an acceptable oil) or ion exchange resins, or as sparingly soluble derivatives, for example, as a sparingly soluble salts.

Additionally, compounds can be delivered using sustained-release systems, such as semipermeable matrices of solid polymers containing the at least one compound. Various sustained-release materials have been established and are well known by those of ordinary skill in the art. Sustained-release capsules may, depending on their chemical nature, release the compound following administration for a few weeks up to over 100 days.

A. Treatment of Cancer

Artemisinin and its derivatives such as dihydroartemisinin and artesunate have anti-cancer activity. The anti-cancer effects of artemisinin and its derivatives have been linked to iron-induced activation of the endoperoxide group of artemisinin to generate toxic radical species in the cells. Artemisinin activity against cancer can be enhanced by delivering the compound to the cellular iron uptake pathway.

"Cancer" refers to a class of diseases in which a group of cells display uncontrolled growth (excessive division), invasion and/or destruction of adjacent tissues, and in some instances, metastasis. "Metastasis" refers to the spread of cancer cells from their original site of proliferation to another part of the body where a new tumor can be formed. A "tumor" is a swelling formed by the abnormal growth of cancer cells. Tumors can show partial or complete lack of structural organization and functional coordination with the normal tissue, and usually form a distinct mass of tissue. Cancers that can be treated using the compounds disclosed herein include, without limitation, adrenal cancer, bladder cancer, blood cancer, bone cancer, bone marrow cancer, brain cancer, breast cancer, carcinomas, cervical cancer, colon cancer, colorectal cancer, ear, nose and throat (ENT) cancer, endometrial cancer, esophageal cancer, gastrointestinal cancer, gliomas, gum cancer, head cancer, Hodgkin's lymphomas, intestinal cancer, kidney cancer, leukemias, liver cancer, lung cancer, lymph node cancer, lymphomas, malignant cancers, melanomas, nasopharynx cancer, neck cancer, neoplastic cancers, neuroblastomas, non-Hodgkin's lymphomas, ovarian cancer, pancreatic cancer, prostate cancer, rectal cancer, sarcomas, seminomas, skin cancer, stomach cancer, teratomas, testicular cancer, thyroid cancer, tongue cancer, and uterine cancer.

In the context of cancers, effective amounts and therapeutically effective amounts can decrease the number of metastases, decrease the number of tumor cells, decrease tumor volume, increase life expectancy, induce apoptosis of cancer cells, induce cancer cell death, induce chemo- or radiosensitivity in cancer cells, inhibit angiogenesis near cancer cells, inhibit cancer cell proliferation, inhibit tumor growth, prevent metastasis, prolong a subject's life, reduce cancer-associated pain, reduce the number of metastases, and/or reduce relapse or re-occurrence of the cancer following treatment.

In particular embodiments, a compound or pharmaceutical composition disclosed herein can have an $IC_{50}$ against a cancer cell line of between 0.01 µM and 30 µM, between 0.1 µM and 20 µM, between 1 µM and 30 µM, at most 26 µM, at most 1 µM, at most 0.1 µM, at most 10 µM, or at most 20 µM. In one embodiment, this $IC_{50}$ is for breast cancer cells.

B. Treatment of Parasitic Infections

Compounds disclosed herein can be used to treat parasitic infections. Parasitic infections include, without limitation, those caused by *Leishmania, Toxoplasma, Plasmodia, Theileria, Acanthamoeba, Anaplasma, Giardia, Trichomonas, Trypanosoma, Coccidia,* and *Babesia*. For example, parasitic infections include those caused by *Trypanosoma cruzi, Eimeria tenella, Plasmodium falciparum, Plasmodium vivax, Plasmodium ovale, Cryptosporidium parvum, Naegleria fowleri, Entamoeba histolytica, Balamuthia mandrillaris, Entameoba histolytica, Schistostoma mansoni, Leishmania (L.) donovani, L. infantum, L. chagasi, L. mexicana, L. amazonensis, L. venezuelensis, L. tropics, L. major, L. minor, L. aethiopica, L. Biana braziliensis, L. (V.) guyanensis, L. (V.) panamensis, L. (V.) peruviana, Trypanosoma brucei rhodesiense, T. brucei gambiense, Giardia intestinalis, G. lambda, Toxoplasma gondii, Trichomonas vaginalis, Pneumocystis carinii, Acanthamoeba castellani A. culbertsoni, A. polyphaga, A. healyi, (A. astronyxis), A. hatchetti, A. rhysodes,* and *Trichinella spiralis*.

1. Treatment of Malaria

Artemisinin and its derivatives have been used for malaria treatment in humans. The anti-malarial effects of artemisinin and its derivatives have been linked to iron-induced activation of the endoperoxide group of artemisinin to generate toxic radical species in the cells. Artemisinin activity against malaria can be enhanced by delivering the compound to the cellular iron uptake pathway of infected cells.

Malarial infections can be caused by any malaria parasite including, without limitation, *Plasmodium (P.) vivax, P. ovale, P. falciparum, P. malariae, P. yoelii, P. bubalis, P. juxtanucleare, P. circumflexum, P. relictum, P. vaughani, P. minasense, P. agamae, P. dominicum; P. knowlesi, P. simiovale,* and *P. brasilianum. P. falciparum P. vivax, P. ovale,* and *P. malariae* constitute the major human *P.* species.

The *P.* parasite is carried by mosquitoes and is introduced into a human when a mosquito bites the human injecting parasites along with anticoagulants. Sporozoite forms of the parasite invade liver hepatocytes, where the parasites are relatively shielded from the immune system and undergo asexual development during the next seven to ten days. During this time, the parasite number increases by 20,000 to 30,000-fold. The parasites are next released from the liver into the blood in the form of merozoites where they quickly enter red blood cells. The red blood cell stage of the disease is responsible for the main symptoms of malaria, including cyclic fevers. In the liver, an erythrocytic cycle becomes established with continued multiplication and liver cell release of merozoites. Some malaria parasites in the body differentiate into gametocytes, or sexual erythrocytic stages. These gametocytes can be ingested by biting mosquitos, leading to new sporogenic cycles and injection of the sporozoites into another human, thereby spreading the disease from human to human.

In the context of malaria, effective amounts and therapeutically effective amounts can interfere with progression between any of the stages of infection described above. For example effective amounts and therapeutically effective amounts can reduce or prevent sporozoite invasion of liver hepatocytes, prevent or reduce asexual development of sporoziotes within the liver, prevent or reduce merozoite release from the liver into the blood, prevent or reduce merozoite entry into red blood cells, and/or prevent or reduce symptoms associated with malaria, including cyclic fevers and death.

2. Treatment of *Coccidia* Infection

Compounds and pharmaceutical compositions disclosed herein can also be used to treat *coccidia* infection. Coccidiosis is an intestinal disease that affects several animal species and presents a particularly important problem in the raising of poultry and cattle. Damage is incurred by the rapid multiplication of the parasite in, and the subsequent rupture of, cells of the intestinal lining. Exemplary *coccidia* species include *Eimeria (E.) acervulina, E. aubemensis, E. bovis, E. brunetti, E. hagani, E. maxima, E. mitis, E. necatrix, E. praecox, E. tenella*, and *E. zuemii*.

Parasites causing *coccidia* infection undergo various stages of development. Infection gives rise to a microscopic egg (an oocyst), which is passed out in manure. Under proper conditions, the oocyst develops within three to seven days to form a sporulate oocyst, which is capable of infecting other livestock. The sporulated oocyst contains eight bodies (sporozoites), each of which is capable of entering a cell in the animal's intestine. When sporozoites enter intestinal cells, they divide several times, each division resulting in offspring capable of entering another intestinal cell. Male and female cells are produced. The male fertilizes the female to produce an oocyst, which in turn ruptures the intestinal cell and is passed in the manure. Thousands of oocysts may be passed in the manure of infected animals. Oocysts are resistant to environmental stresses and contaminate feed and water, infecting other animals.

Within the context of the current disclosure, anticoccidial compositions within bird feed and/or drinking water could be administered during the whole growing period of broiler chickens to prevent infections caused by E. parasites.

Effective amounts and therapeutically effective amounts against *coccidia* infection include those that reduce or prevent any stage of the parasite's development cycle. For example, effective amounts and therapeutically effective amounts can reduce or prevent development of oocysts, reduce the number of oocysts passed out in manure, reduce or prevent oocyst development into sporulate oocysts following excretion, reduce or prevent sporulated oocyst entry into animal's intestine, reduce or prevent division of sporozoites following entry into intestinal cells, reduce or prevent fertilization of female sporozoites, reduce or prevent rupture of intestinal cells, and/or reduce or prevent the symptoms of *coccidia* infection including caecal weight gain; overall weight loss and/or death.

C. Treatment of Yeast Infections

Yeast infections usually result from an overgrowth of a species of fungus called *Candida (C.) albicans*. They can occur on the skin, under nails or mucous membranes of the mouth, vagina, bronchi, and lungs.

Yeast infections include, but are not limited to, infections caused by *Brettanomyces (B.) clausenii, B. custerii, B. anomalous, B. naardenensis, C. himilis, C. intermedia, C. saki, C. solani, C. tropicalis, C. versatilis, C. bechii, C. famata, C. lipolytica, C. stellata, C. vini, Debaromyces hansenii, Dekkera intermedia, Dekkera bruxellensis, Geotrichium sandidum, Hansenula fabiani, Hanseniaspora (H.) uvarum, Hansenula anomala, H. guillermondii, H. vinae, Kluyveromyces lactis, Kloekera apiculata, Kluveromyces (K.) marxianus, K. fragilis, Metschikowia pulcherrima, Pichia guilliermodii, Pichia orientalis, Pichia fermentans, Pichia memranefaciens, Rhodotorula Saccharomyces (S.) bayanus, S. cerevisiae, S. dairiensis, S. exigus, S. uinsporus, S. uvarum, S. oleaginosus, S. boulardii, S. ludwigii, S. pombe, Torulaspora delbruekii, Torulopsis stellata, Zygoaccharomyces bailli* and *Zygosaccharomyces rouxii*.

Regarding *Candida* particularly, in the yeast state *Candida* is a non-invasive, sugar-fermenting organism. While in the fungal state, however, *Candida* is invasive and can produce rhizoids, which are very long root-like structures. Rhizoids can penetrate mucosa or intestinal walls, leaving microscopic holes and allowing toxins, undigested food particles and bacteria and yeast to enter the bloodstream.

Certain physiological environmental conditions can promote the overgrowth of the fungus in particular areas of the body. For example, the fungus may proliferate excessively in the mouth resulting in a condition known as thrush or may grow excessively in the genital area resulting in what is commonly referred to as a genital yeast infection. Although men are susceptible to genital yeast infections, women are particularly susceptible to them. The symptoms of genital yeast infections include itching, burning, redness, and irritation of the genital area. In women, severe vaginal yeast infections may cause swelling of the vulva and result in inflammation of the urinary opening. Additionally, women may experience abnormal vaginal discharge.

Effective amounts and therapeutically effective amounts against yeast infection include those that reduce or prevent production of rhizoids, reduce or prevent rhizoid penetration of mucosa or intestinal walls, reduce or prevent thrush; reduce or prevent genital yeast infections, reduce or prevent symptoms of genital yeast infections including, without limitation, itching, burning, redness, irritation, swelling of the vulva, inflammation of the urinary opening and/or abnormal vaginal discharge.

EXAMPLES

Example 1

Compound Synthesis

Air-sensitive and moisture-sensitive reactions were carried out in oven-dried glassware sealed with rubber septa under a positive pressure of dry nitrogen. Similarly sensitive liquids and solutions were transferred via syringe. Reactions were stirred using Teflon-coated magnetic stir bars. Anhydrous solvents were obtained from commercial sources. Analytical thin layer chromatography was performed with 0.25 mm silica ger 60 F plates with 254 nM fluorescent indicator. Plates were visualized by ultraviolet light or by treatment with vanillin/sulphuric acid in ethanol by gentle heating. Chromatographic purification of products was accomplished by flash chromatography. NMR spectra were measured on Bruker (300 MHz and 500 MHz) nuclear magnetic resonance spectrometers. Solvents are indicated in text. Mass spectra (MS) were measured by Bruker Esquire Ion Trap mass at chemistry department in the University of Washington. Bruker AutoFlex II MALDI-MS was obtained at the Medicinal Chemistry Mass Spectrometry Facility in the University of Washington.

DMEM high glucose culture media, 0.25% Trypsin-EDTA solution, Dulbecco's phosphate buffered saline, 3-(4,5-dimethylthiazol-2-yl)-2,5-diphenyltetrazolium bromide (MTT) and Trypan blue (0.4%) solution were purchased from Sigma-Aldrich. Fetal bovine serum was obtained from Invitrogen Corp. Other chemicals and reagents were obtained from Sigma-Aldrich. BT474 and MDA-MB-231 cells were obtained from the American Type Culture Collection (Manassas, Va.).

Example 1A

Synthesis of Compound 2

10β-(3-Oxopropyl)-deoxoartemisinin. To a stirred solution of 1 (175 mg, 0.54 mmol) in dry benzene (3 mL) and dry dimethyl sulfoxide (3 mL) were added pyridine (150 μL, 1.93 mmol), trifluoroacetic acid (30 μL, 0.39 mmol), and N,N-dicyclohexylcarbodiimide (462 mg, 2.25 mmol) at room temperature. The mixture was stirred for 18 hr at room temperature, then, $CH_2Cl_2$ (20 mL) was added to the mixture, which was filtered. The filter cake was washed with $CH_2Cl_2$ (20 mL). The combined filtrate and washings were washed with water and brine. The $CH_2Cl_2$ solution was dried over $Na_2SO_4$ and concentrated in vacuo. The residue was passed through silica gel (Hexane:EtoAc=7:3) to give Compound 2 as a white solid (160 mg, 0.49 mmol, 91% yield).
$^1$H NMR (300 MHz, CDCl3) δ 9.86 (1H, s, CHO), 5.27 (1H, s, H-12), 4.10-4.17 (1H, m, H-10), 2.62-2.68 (1H, m, H-9), 2.33 (1H, m, H-4a), 2.59-0.88 (23H, m) including 1.41 (3H, s, 3Me), 0.88-1.04 (6H, m, 6Me, 9Me). LRMS (ESI), m/z [M+H]+ 325.4.

Example 1B

Synthesis of Compound 3

A solution of 1 (163 mg, 0.5 mmol), $Ph_3P$ (225 mg, 1 mmol), Phthalimide (147 mg, 1 mmol), and DIAD (150 mg, 0.8 mmol) in THF (20 mL) was heated to 50° C. for 4 hr, and cooled to room temperature. Water (20 mL) was added, the mixture was extracted with $CH_2Cl_2$ (20 mL×3). The organic phase dried over $Na_2SO_4$, and concentrated under reduced pressure to give light yellow oil, then purify by flash column chromatography (silica gel, Hexane/EtOAc) produced product 3 as white solid (205 mg, 90% yield).
$^1$H NMR (300 MHz, CDCl3) δ 7.84 (2H, q, J=3, H-Py), 7.71 (2H, q, J=3, H-Py), 5.30 (1H, s, H-12), 4.18-4.25 (1H, m, H-10), 3.70-3.80 (2H, m, CH2), 2.61-2.68 (1H, m, H-9), 2.37-0.75 (23H, m) including 1.41 (3H, s, 3Me), 0.75-1.00 (6H, m, 6Me, 9Me). LRMS (ESI), m/z [M+H]+ 456.3.

Example 1C

Synthesis of Compound 4

10β-(3-Aminopropyl)-deoxoartemisinin. A solution of 3 (205 mg, 0.45 mmol) and $NH_2NH_2.H_2O$ (192 mL, 2.5 mmol, 64%-65% solution) in ethanol (15 mL) was stirred overnight at 50° C., then, filtered and the filtrate evaporated, the purified by flash column chromatography (silica gel, dichloromethane/methanol/Ammunioum hydroxyl=100:10:0.2) to give 4 as white solid (110 mg, 0.34 mmol, 75% yield).
$^1$H NMR (500 MHz, CDCl3) δ 5.34 (1H, s, H-12), 4.18-4.22 (1H, m, H-10), 2.81 (2H, t, J=5 Hz CH2NH2), 2.67-2.72 (1H, m, H-9), 2.59-0.88 (23H, m) including 1.44 (3H, s, 3Me), 0.86-1.07 (6H, m, 6Me, 9Me). MS (ESI), m/z [M+H]+ 326.4.

Example 1D

Synthesis of Compound 6a

A solution of 2 (35 mg, 0.11 mmol), 4 (0.35 mg, 0.11 mmol) and trifluoroacetic acid 5a (8 μL, 0.11 mmol) in 0.5 mL anhydrous methanol was stirred at room temperature for 30 min. Then, methyl isocyanoacetate (19 μL, 2 mmol) was added. After stirring overnight, water (10 mL) was added to quench the reaction, the mixture was extracted with $CH_2Cl_2$ (10 mL×2), separated, the organic phase was dried over $Na_2SO_4$ and concentrated in vacuo to give light yellow oil. The crude product was purified by flash column chromatography (silica gel, Hexane/EtOAc=5:3) to got product 6a as white solid (63 mg, 0.075 mmol, 68% yield).
$^1$H NMR (500 MHz, CDCl$_3$) δ 5.29-5.19 (3H, 2×H-12), 4.73-3.40 (7H, m, 2×H-10, CH, NH, CH$_2$, Me), 2.64-0.72 (56H, m) including 1.34, 1.20 (3H, 2×3Me), 0.94-0.72 (12H, m, 2×6Me, 2×9Me). MS (ESI), m/z [M+H]+ 845.7.

Example 1E

Synthesis of Compound 6b

Compound 2 (32 mg, 0.1 mmol), Compound 4 (32 mg, 0.1 mmol), methyl isocyanoacetate (18 μL, 0.2 mmol), and Compound 5b (12 mg, 0.1 mmol) were reacted. The crude product was purified by flash column chromatography (silica gel, Hexane/EtOAc=5:6) to get product 6b as a white solid (44 mg, 0.052 mmol, 52% yield).
$^1$H NMR (500 MHz, CDCl$_3$) δ 7.68, 7.60 (H, benzonic acid), 7.45 (2H, benzonic acid), 7.44 (2H, benzonic acid), 5.34-4.88 (3H, 2×H-12), 4.18-3.36 (7H, m, 2×H-10, CH, NH, CH$_2$, Me), 2.73-0.74 (56H, m) including 1.41, 1.29 (3H, 2×3Me), 1.05-0.75 (12H, m, 2×6Me, 2×9Me). MS (ESI), m/z [M+H]+ 853.9.

Example 1F

Synthesis of Compound 6c

Compound 2 (22 mg, 0.07 mmol), Compound 4 (22 mg, 0.07 mmol), methyl isocyanoacetate (14 ul, 0.14 mmol), and Compound 5c (12 mg, 0.07 mmol) were reacted. The crude product was purified by flash column chromatography (silica gel, Hexane/EtOAc=5:6) to get product 6c as a white solid (21 mg, 0.023 mmol, 33% yield).
$^1$H NMR (500 MHz, CDCl$_3$) δ 7.14 (H, td, J=5, 2,3-dimethoxybenzoic acid), 6.97 (H, q, J=5, 2,3-dimethoxybenzoic acid), 6.84 (H, t, J=10, 2,3-dimethoxybenzoic acid), 5.34-5.02 (3H, 2×H-12), 4.20-3.21 (14H, m, 2×H-10, CH, NH, CH$_2$, 2,3-dimethoxybenzoic acid, 2×Me), 2.73-0.74 (56H, m) including 1.44, 1.42 (3H, 2×3Me), 1.05-0.78 (12H, m, 2×6Me, 2×9Me). MS (ESI), m/z [M+H]+ 913.9.

Example 1G

Synthesis of Compound 6d

Compound 2 (22 mg, 0.07 mmol), Compound 4 (22 mg, 0.07 mmol), methyl isocyanoacetate (14 μL, 0.14 mmol), and Compound 5d (12 mg, 0.07 mmol) were reacted. The crude product was purified by flash column chromatography (silica gel, Hexane/EtOAc=1:1.5) to get product 6d as a white solid (14 mg, 0.016 mmol, 22% yield).
$^1$H NMR (500 MHz, CDCl$_3$) δ 7.40 (2H, q, J=5, 4-(dimethylamino)benzoic acid), 6.70 (2H, q, J=5, 4-(dimethylamino)benzoic acid), 5.33, 5.19, 5.14 (3H, 2×H-12), 4.75-3.37 (8H, m, 2×H-10, CH, NH, CH$_2$) including 3.77, 3.76 (3H, Me), 3.03 (6H, 2×4-(dimethylamino)benzoic acid Me) 2.73-0.78 (56H, m) including 1.44, 1.40 (3H, 2×3Me), 1.05-0.78 (12H, m, 2×6Me, 2×9Me). MS (ESI), m/z [M+H]+ 897.1.

Example 1H

Synthesis of Compound 6e

Compound 2 (22 mg, 0.07 mmol), Compound 4 (22 mg, 0.07 mmol), methyl isocyanoacetate (14 μL, 0.14 mmol), and Compound 5e (12 mg, 0.07 mmol) were reacted. The crude product was purified by flash column chromatography (silica gel, Hexane/EtOAc=1:1.5) to get product 6e as a white solid (33 mg, 0.039 mmol, 55% yield).

$^1$H NMR (500 MHz, CDCl$_3$) δ 9.00-8.86 (2H, m, pyrazine-2-carboxylic acid), 8.67-8.49 (2H, m, pyrazine-2-carboxylic acid), 5.30-5.5.03 (3H, m, 2×H-12), 4.47-3.14 (8H, m, 2×H-10, CH, NH, CH$_2$) including 3.71 (3H, s, Me), 2.37-0.70 (56H, m) including 1.34, 1.21 (3H, s, 2×3Me), 1.00-0.70 (12H, m, 2×6Me, 2×9Me). MS (ESI), m/z [M+H]$^+$ 855.8.

Example 1I

Synthesis of Compound 6f

Compound 2 (22 mg, 0.07 mmol), Compound 4 (22 mg, 0.07 mmol), methyl isocyanoacetate (14 μL, 0.14 mmol), and Compound 6f (9 mg, 0.07 mmol) were reacted. The crude product was purified by flash column chromatography (silica gel, Hexane/EtOAc=1:1) to get product 6f as a white solid (20 mg, 0.023 mmol, 33% yield).

$^1$H NMR (500 MHz, CDCl$_3$) δ 8.14 (2H, d, J=5, p-nitrophenol), 6.91 (2H, d, J=5, p-nitrophenol), 5.35-5.24 (3H, t, 2×H-12), 4.57-3.47 (8H, m, 2×H-10, CH, NH, CH$_2$) including 3.74 (3H, s, Me), 2.68-0.82 (56H, m) including 1.42, 1.38 (3H, s, 2×3Me), 1.04-0.88 (12H, m, 2×6Me, 2×9Me). MS (ESI), m/z [M+H]$^+$ 870.8.

Example 1J

Synthesis of Compound 6h

Compound 2 (22 mg, 0.07 mmol), Compound 4 (22 mg, 0.07 mmol), methyl isocyanoacetate (14 μL, 0.14 mmol), and Compound 5g (12 mg, 0.07 mmol) were reacted. The crude product was purified by flash column chromatography (silica gel, Hexane/EtOAc=5:4) to get product 6g as a white solid (21 mg, 0.023 mmol, 33% yield).

$^1$H NMR (300 MHz, CDCl$_3$) δ 7.04-6.97 (1H, m, tetrafluorophenol), 5.34-5.27 (3H, t, 2×H-12), 4.51-3.95 (5H, m, 2×H-10, CH, NH, CH$_2$), 3.51-0.90 (56H, m) including 1.44, 1.39 (3H, 2×3Me), 1.04-0.88 (12H, m, 2×6Me, 2×9Me). MS (ESI), m/z [M+H]$^+$ 883.339.

Example 1K

Synthesis of Compound 7

Compound 2 (64 mg, 0.2 mmol), Isopropylamine (25 μL, 0.3 mmol), methyl isocyanoacetate (32 μL, 0.4 mmol), and benzonic acid (24 mg, 0.2 mmol) were reacted. The crude product was purified by flash column chromatography (silica gel, Hexane/EtOAc=1:1) to get product 7 as a white solid (44 mg, 0.023 mmol, 38% yield).

$^1$H NMR (300 MHz, CDCl$_3$) δ 7.45-7.39 (5H, m, benz), 5.30 (1H, s, H-12), 5.40 (1H, s, H-12), 4.17-3.87 (5H, m, H-10, isopropylamine CH, CH, NH, CH$_2$), 3.74 (3H, OMe), 2.71-0.86 (27H, m) including 1.41, 1.39 (3H, 3Me), 1.04-0.88 (12H, m, 6Me, 9Me, isopropyl 2×Me). MS (ESI), m/z [M+H]$^+$ 587.5.

Example 2

Anti-Cancer Effects

Example 2A

In Vitro Toxicity

In vitro toxicity of the compounds described herein were tested on two breast cancer cell lines, MDA-MB-231 and BT-474. These cell lines represent triple negative and HER2-positive breast cancers, respectively. BT474 cell and MDA-MB-231 cells were maintained in DMEM media supplemented with 10% v/v FBS. On reaching confluency (1×10$^6$ cells/mL in a 25 mL flask), 1×10$^6$ cells were seeded in 25 mL of fresh supplemented media. The cells were incubated under humidified air containing 5% CO2 at 37° C. Cell density was kept below 1×10$^6$ cells/mL to ensure exponential growth and to avoid differentiation. Cells were only used between passages 5 and 15 to prevent cell differentiation.

A standard MTT assay was used to determine the cell viability at 48 hr after an artemisinin derivative was added to the culture medium. Cell viability was above 95% for all experiments. The viable cell count was based on trypan blue exclusion from the cells and was performed in a hemocytometer using a light microscope. To 50 μL of cells was added 20 μL of trypan blue 0.4% solution and 30 μL D-Hanks solution was counted. During experiments cells were exposed to drug stock solutions which were made up in 100% DMSO and the final solvent concentration was 1% v/v in each incubation. Each concentration in every experiment was carried out in triplicate.

As positive controls, artesunate and artemisinin dimer succinate were included. Artemisinin dimer succinate has been shown to be up to 500 times more potent than artemisinin monomers such as artesunate when tested on a panel of NCI 60 cell lines. With MDA-MB-231 cell line, artemisinin dimers showed significantly higher potency than artesunate. Dimer 6f was only 5 times less potent than artemisinin dimer succinate. With BT-474 cell lines, all the artemisinin dimers showed high activities. For example, dimer 6h showed an IC$_{50}$ value of 12 nM, approximately 8 times more potent than artemisinin dimer succinate.

The cytotoxicity of artemisinin dimers, dimer-2Py, was evaluated against a panel of four PCa cell lines, DU 145, PC-3, C4-2, and LNCaP. While dimer-2Py was highly potent, dihydroartemisinin, a monomeric artemisinin, showed a negligible activity under the same conditions. Dimer-2y decreased survivin protein levels in all of the prostate cancer cell lines. Furthermore, dimer-2Py also induced the loss of androgen receptor (AR) and prostate specific antigen (PSA) expression in the C4-2 and LNCaP cells. Dimer-ON-2Py, an analog of dimer-2Py where the hydrazone linkage is replaced by an oxime, showed significantly reduced cytotoxicity.

When tested on HL60 cell line, both phosphate-linked and amide-linked dimers showed IC$_{50}$ of low nM ranges while carbonate-linked and urea-linked dimers were essentially devoid of cytotoxicity.

Example 2B

MTT Cell Viability Assay

BT474 (2000 cells/100 μL) or MDA-MB-231 cells (7500 cells/100 μL) were seeded on a 96 well plate respectively, and incubated for 24 hr at 37° C. The medium was removed, and replaced it with 200 μL of the complete medium containing artemisinin derivatives. The cells were incubated for 48 hr at 37° C., the medium was removed, and replaced it with 100 μL of fresh complete medium. 10 μL of 12 μM MTT stock solution (D-Hanks) was added to each well. After incubating for 3 hr at 37° C., formazan crystals were solubilized in 50 μL of DMSO and absorbance was measured at 570 nm with BIO-RAD model 680 microplate reader. All data were analyzed using Microsoft Excel. $IC_{50}$ values were determined with Graphpad Prism 5.

The following Table illustrates the different artemisinin monomers and dimers described herein.

| Compound | MDA MB 231 $IC_{50}$ (μM) | BT474 $IC_{50}$ (μM) | MCF-10A $IC_{50}$ (μM) | Selectivity MDA MB 231 | Selectivity BT474 |
|---|---|---|---|---|---|
| Artesunate | 46 | 7.8 | 21 | 0.46 | 2.7 |
| Artemisinin dimer succinate | 0.24 | 0.10 | 21 | 88 | 210 |
| 6a | 19 | 6.6 | 4.6 | 0.24 | 0.70 |
| 6b | 11 | 0.79 | 5.0 | 0.45 | 6.3 |
| 6c | 12 | 5.8 | 5.7 | 0.48 | 0.98 |
| 6d | 12 | 0.88 | 15 | 1.3 | 17 |
| 6e | 26 | 1.7 | 25 | 0.96 | 15 |
| 6f | 1.2 | 0.096 | 47 | 39 | 490 |
| 6h | 2.3 | 0.012 | 98 | 43 | 8200 |
| 7 | >100 | >100 | >100 | — | — |

As illustrated in FIGS. 1(A)-(E) and 2(A)-(E), there can be a large difference in artemisinin dimer activity. This difference in activity exists even though the average distance between two artemisinin units remained the same. Artemisinin is an iron-dependent alkylating agent, and artemisinin dimers may be involved in crosslinking of key biomolecules that are involved in cellular proliferation. The length and functional groups of the linker may play a role in the association of artemisinin dimers and their cellular target(s).

Example 2C

In Vivo Tumoricidal Effects of the Compounds

The mouse xenograft, bioluminescence model employs the U87 GMB cell line (ATCC), which has been retrovirally transfected with the coding sequence for luciferase in a pMMP vector. Established U87-Luciferase cell lines are harvested in mid-logarithmic growth phase, resuspended as 50,000 cells in 10 μl PBS, and introduced into mice brain using stereotactic guidance (2 mm lateral and posterior to the bregma, 3 mm below dura). Mice are given D-luciferin (Xenogen, Alameda, Calif.) intraperitoneal injections and imaged with the IVIS imaging system (Xenogen) on post-surgery day 5 and 10.

For each compound tested, a group of 20 mice are implanted with U87-Luciferase and surveyed on post-implant day 5 and 10, out of which 20-26 mice are expected to have uptake of the implanted tumor (Rubin et al., (2003) Proc. Natl. Acad. Sci. USA, 100: 13513-13518). Mice with U87-Luciferase tumor uptake are then surgically implanted with an intraventricular catheter and Alzet pump 1007D. These mice are then divided into two groups: Group 1: treated with control vehicle (25% DMSO) Group 2: treated with compound (15 mg/kg) intraventricularly.

The intraventricular catheter is placed contra-lateral to the tumor implant site to minimize the effect of tumor growth on stereotactic coordinates. Injections are carried out 4 days after intraventricular administration to allow for sensitization. The mice are imaged on day 15 and 20 after initial tumor implant. Comparison of tumor growth is determined using LIVING IMAGE software package (Xenogen). The experiment is repeated for each compound (6a, 6b, etc.). Treated mice have smaller tumors.

Example 2D

Efficacy of the Compounds in Sensitizing Ovarian Tumors to Anti-Neoplastic Agents in an Animal Model A number of animal models for ovarian cancer are known in the art. For example, Connolly et al. ((2003) Cancer Research, 63, 1389-1397) discloses methods of developing epithelial ovarian cancer in mice by chimeric expression of the SV40 Tag under control of the MISIIR promoter. In another example (Liu et al., (2004) Cancer Research 64, 1655-1663) discloses the introduction of human HRAS or KRAS oncogenes into immortalized human ovarian surface epithelial cells, which form s.c. tumors after injection into immunocompromised mice. These mice models provide useful means to test the efficacy of the compounds in sensitizing ovarian tumors to anti-neoplastic agents. 6 mice are used per group. To test the efficacy of cisplatin, alone or in combination with the compounds, the following groups are used: Group 1: treated with control vehicle; Group 2: treated with cisplatin, 4 mg/kg; Group 3: treated with compound at 5 mg/kg Group 4: treated with cisplatin, 4 mg/kg, and compound, 5 mg/kg. The injections are repeated two days later.

All treatments are started a week after tumor inoculation. Mice are treated for 10 cycles in total, and sacrificed for tumor nodule counting two weeks (on day 50) after discontinuation of treatment. Upon sacrifice, antitumor activity in each group is evaluated by counting the number of tumor nodules in the peritoneal cavity, measuring the diameter of the tumors, measuring the volume of the ascites and qualitatively observing the color of the peritoneal wall as an indication of the degree of tumor-induced vascularization. Toxicity is evaluated by qualitative observation of the general appearance and behavior of the mice prior to sacrifice and by measuring their body weight at various intervals during the course of the treatments. The experiment is repeated for each compound (6a, 6b, etc.). Each of the compounds alone is shown to provide an effective anti-cancer treatment and each of the compounds augments the effects of the co-administered anti-cancer agent.

Example 2E

Clinical Evaluation of Treatment of Recurrent Mullerian Malignancies with the Compounds A Phase I open-label, dose-escalation safety study is conducted in patients with recurrent carcinoma of mullerian origin, less than 12 months from prior platinum-based chemotherapy. Compound is administered orally. A treatment cycle is 28 days with compound administration beginning on day 1 followed by a 28-day follow-up period. Decisions regarding dose escalation and Dose Limiting Toxicity determination are made at the end of the 4 week cycle. Patients who tolerate treatment without evidence of disease progression are eligible for additional cycles of compound treatment.

Initially three patients will be entered in the first dose level. The initial dose level will be 900 mg. If none has Dose Limiting Toxicity (DLT), then the next 3 patients get dose level 2. If a DLT occurs at any dose level, three additional patients are enrolled to that dose level. If two DTLs occur at that dose level, then it is declared above the Maximum Tolerated Dose (MTD) and the MTD is defined at the previous dose level. No intrapatient dose escalations are made.

Definition of Dose-Limiting Toxicity (DLT). The determination of DLT for purposes of assessing dose escalation is defined using the NCI CTC version 3.0 criteria with consideration of known and accepted toxicities of carboplatin.

Response and progression are evaluated using the international criteria proposed by the Response Evaluation Criteria in Solid Tumors (RECIST) Committee (JNCI 92(3):205-216, 2000). Changes in the largest diameter of the tumor lesions are used in the RECIST criteria. Lesions are either measurable or nonmeasurable using the criteria listed below.

Guidelines for Evaluation of Measurable Disease. At baseline, tumors lesions are categorized as follows: (1) measurable—lesions that can be accurately measured in at least one dimension as 20 mm with conventional techniques or as 10 mm with spiral CT or (2) nonmeasurable—all other lesions All measurements are recorded in metric notation. All baseline evaluations are performed as closely as possible to the beginning of treatment and never more than 4 weeks before the beginning of treatment. Non-measurable disease includes the following: bone lesions, leptomeningeal disease, ascites, pleural/pericardial effusion, abdominal masses that are not confirmed and followed by imaging techniques, and cystic lesions.

Clinically detected lesions are considered measurable when they are superficial (i.e. skin nodules and palpable lymph nodes). All skin lesions are documented with color photography, including a ruler to estimate the size of the lesion.

Chest X-Ray. Although lesions on chest x-ray are acceptable as measurable lesions when they are clearly defined, a CT is preferable.

Computed Tomography (CT) and Magnetic Resonance Imaging (MRI). CT and MRI are the best available (and most reproducible) methods for measuring target lesions selected for response assessment. Conventional CT and MRI are performed with contiguous cuts of 10 mm or less in slice thickness.

Tumor Markers. Tumor markers alone are not used to assess response. However, if markers are initially above the upper limit, they must return to normal levels for a patient to be considered in complete clinical response when all tumor lesions have disappeared.

Cytology, Histology. These techniques are used to differentiate between partial responses (PR) and complete responses (CR) in rare cases where residual lesions in tumor types can contain benign components. The cytological confirmation of the neoplastic origin of any effusion that appears or worsens during treatment when the measurable tumor has met criteria for response or stable disease is mandatory to differentiate between response or stable disease and progressive disease.

Evaluation of Target Lesions. Criteria to evaluate lesions have been adapted from the original WHO Handbook, taking into account the measurement of the longest diameter only for all target lesions: complete response—the disappearance of all target lesions; partial response—at least a 30% decrease in the sum of the longest diameter of target lesions, taking as reference the baseline sum longest diameter; progressive disease—at least a 20% increase in the sum of the longest diameter of target lesions, taking as reference the smallest sum longest diameter recorded since the treatment started or the appearance of one or more new lesions; stable disease— neither sufficient shrinkage to qualify for partial response nor sufficient increase to qualify for progressive disease, taking as reference the smallest sum longest diameter since the treatment started.

Studies will be undertaken for each compound (6a, 6b, etc.) and each will show acceptable safety profiles and anti-tumor effects.

Example 3

Anti-Malaria Effects

Example 3A

The in vivo anti-malarial activity of the compounds is assessed using the *P. chabaudi* and *P. berghei* models by the standard 4-day Peters' test including pyrimethamine as a comparator drug in each experiment. Briefly, 20 gr CD1 male mice (Charles Rivers, UK) are kept in specific pathogen-free conditions and fed ad libitum. For oral administration, compounds are dissolved in standard suspending formula (SSV) [0.5% sodium carboxymethylcellulose, 0.5% benzyl alcohol, 0.4% Tween 80, 0.9% NaCl (all Sigma)] and for intraperitoneal or subcutaneous administration compounds are dissolved in 0.5% w/v hydroxypropylmethylcellulose, 0.4% v/v Tween 80, 0.5% V/v benzyl alcohol in de-ionised water. Mice are infected intravenously with $4 \times 10^6$ infected red cells and treated orally (p.o.) with 0.2 ml of a solution of the compounds two hours (day 0) and on days 1, 2 and 3 post-infection. Parasitaemia is determined by microscopic examination of Giemsa stained blood films taken on day 4. Microscopic counts of blood films from each mouse are processed using GraphPad Prism 4 (GraphPad Software, Inc., CA, USA) and expressed as percentages of inhibition from the arithmetic mean parasitaemias of each group in relation to the untreated group. Compounds are tested in an initial screening at 30 mg/kg/day against *P. chabaudi* AS (non-resistant) over the period described and percentages of inhibition calculated in relation to the untreated controls. Compounds giving 80% inhibition or above are then tested in the same model under a range of doses over the period described in order to obtain dose response curves and calculate their $ED_{50}$ and $ED_{90}$ values. Compounds giving an $ED_{90}$ at or below the level of the comparator are then selected for testing against *P. chabaudi* ASP (pyrimethamine-resistant strain), and in the lethal *P. berghei* ANKA (non-resistant strain). The results of the in vivo tests against *P. chabaudi* AS show that the compounds have anti-malarial activity in this model and are also tested in *P. chabaudi* ASP and *P. berghei* ANKA. The compounds show $ED_{90}$ values lower than the drug pyrimethamine which displays $ED_{90}$ values of 0.88 mg/kg against *P. chabaudi* AS.

Example 3B

Infection of Mice

Mice are acclimatized for two weeks. They are given food and drink ad libitum. On day 0 (D0), female "Swiss" mice (OF1, 22-26 g) (Charles River Laboratories) are inoculated, by iv injection in the caudal vein, with $10^8$ parasitized erythrocytes suspended in 200 µl of NaCl (0.9%).

The injection of $10^8$ parasitized erythrocytes results, at day 1 (D1), results in a parasitemia level of between 5% and 10%. The infection is maintained by weekly injection of mice with $10^7$ to $10^8$ parasitized erythrocytes suspended in a saline phosphate buffer (0.9%) (infection by intraperitoneal administration).

Compounds are dissolved in a 0.3M phosphate buffer (pH=8.1). The final concentration of compound in the solution is between 40 and 200 mg/l depending on the dose. The compounds are administered ip in a volume of approximately 100 μl depending on the weight of the mouse. Mice are treated with compound by ip administration once a day for 4 days, on days D1, D2, D3 and D4. Four mice are used per dose.

Measurement of the Parasitemia. On the 5th day, a few drops of blood are taken from the tail of the mouse in order to determine the parasitemia by FACS (fluorescence-activated cell sorter) and to perform a blood smear. Parasitemia is first determined by FACS on 20,000 cells. The red blood cells taken for the FACS are fixed with glutaraldehyde and labeled with a fluorochrome (for example, YOYO1®) which labels DNA and therefore only parasitized cells. Parasitemias below 15% are subsequently recounted on smears. The smears are fixed with methanol and then stained with Giemsa stain. The number of parasitized blood cells is counted under a microscope. Parasitemia is expressed as percentage of infected erythrocytes present in the specimen. The $ED_{50}$ and $ED_{90}$ values are determined at D5. Parasitemia is determined from the 1st to the 10th day of treatment, and then at the 15th, 22nd and 47th days.

The mice for which the smear at D5 reveals no trace of parasites will be checked again for at least one month after the end of the treatment, in order to detect any possible upsurge of parasites. The curative dose is the dose of product which ensures the survival of the entire treated batch of animals after one month.

Determination of $ED_{50}$ Values. 0% inhibition corresponds to the mean of the parasitemias observed in the nontreated, infected mice. 100% inhibition corresponds to a very weak or null parasitemia, below 0.01%. $ED_{50}$ values are determined by linear interpolation of the dose-response curve represented in logarithm of concentrations.

The experiment is repeated for each compound (6a, 6b, etc.) and each of the compounds effectively reduce parasitemia when measured after 4 days of treatment.

Example 4

Treatment of *Coccidia* Infection

Example 4A

A liquid compound-containing anticoccidial composition is prepared. 40 broiler chickens 3 weeks-old are fed without any anticoccidial compounds for ten days and then 5 groups are formed. Group 1 remains as a Control Group without anticoccidial compound treatment. Group 2, 3, 4 and 5 receive respectively 0.5, 1, 2 and 4 ml of liquid anticoccidial compound by an oral route, one dose at day 1 and a second dose 8 days later. When birds are 31 days old, they are challenged with 200,000 sporulated oocysts of *E. tenella* by the oral route. The animals are sacrificed 7 days after the challenge to determine lesions according to the well known Johnson and Reid method, based on severity of lesion in a scale ranged from 0 to 4, where 0 mean no lesion and +4 severe lesions, and caecal weight. It is well known that chickens with *E. tenella* infection increase their caecal weights because there is an inflammatory process resulting in a swelling of the caecal wall. All groups with treatment maintain lower caecal weight compared to the caecal weight of the control group. The lesions of the treated groups are lower than in the control group.

Example 4B

Two groups of 25 broiler birds are formed: Group 1 receives 1 ml of compound-containing anticoccidial composition on a daily basis through drinking water or through feed for two weeks. The control group does not receive any treatment. After two weeks, both groups are challenged with 150,000 sporulated oocysts of *E. tenella* per ml by the oral route.

All the animals are sacrificed 7 days later and the caecal lesions are qualified according to the Johnson and Reid method. Mortality is also recorded. In the treated group mortality, caecal weight and lesion score according to Johnson-Reid scale are lower than in the control group.

Example 4C 75 two-week old broiler chickens are divided in two groups of 30 and one group of 15 birds. The groups are identified as Group A, B and C. During the whole experiment the birds consumed food without anticoccidial compound. Group A received 2 ml of liquid anticoccidial compound on a daily basis by drinking water during 4 weeks. After 4 weeks the bird weights are recorded. Group A and B are challenged with 150,000 sporulated oocysts of *E. tenella* per ml by the oral route. Group B receives food with anticoccidial compound after the challenge. Group C remains as a control group. One week later all birds are sacrificed and scored for weight gain and lesions scored by the Johnson and Reid method. There is better weight gain in Group A and B compared to the control group.

Each of the experiments described in Example 4 is repeated for each of the compounds (6a, 6b, etc.). Each of the compounds is effective as an anti-*coccidial* compound.

Example 5

Treatment of Yeast Infections

Example 5A

*C. albicans* (ATCC 10231), *C. tropicalis* (ATCC 28707-amphotericin B-resistant) and *C. tropicalis* (ATCC 750) from stock culture are subcultured on Sabouraud dextrose agar plates for 2 days at 37° C. in ambient air. At least 5 colonies from each of the cultures are inoculated into 3 mL of an appropriate broth and thoroughly mixed. One-tenth mL of this suspension is transferred into 10 mL of the appropriate broth and incubated on a shaking incubator at 37° C. for 5-6 hours. Each suspension of the yeast is then adjusted with sterile saline to contain approximately $5 \times 10^8$ CFU/mL.

Compounds are prepared as 5 mg/mL stock solutions in 100% dimethyl sulfoxide. These are diluted 1:100 into 4 mL of diluted broth media for a starting concentration of 50 μg/mL. An additional 9 tubes are prepared with each containing 2 mL of the appropriate broth medium. Serial doubling dilutions are performed for each set of 10 tubes by transferring 2 mL of compound from the first tube to the second tube, mixing thoroughly, then transferring 2 mL to the next tube and mixing, until the tenth tube. From the tenth tube, 2 mL of mixture is discarded. Each tube is then inoculated with 0.01 mL of the yeast suspension in broth. Tubes are incubated at 37° C. for 20 hours and then scored for visible growth or no visible growth. The MIC is defined as the concentration of compound (μg/mL) that completely inhibits growth of yeast. A positive control (without test compound in broth containing 1% DMSO inoculated with 0.01 mL of the suspension in broth) and a sterility control (only broth containing 1% DMSO) are incubated and evaluated under the same conditions. The MIC determinations and controls are performed in duplicate. Each of the compounds (6a, 6b, etc.) is tested and each is effective to reduce or prevent the presence of yeast.

Example 5B

Rat Vaginal Infection

Oophorectomized female Wistar rats (80-100 g, Charles River Breeding Laboratories) are used. All rats are maintained under pseudoestrus by injection of estradiol benzoate (Amsa Farmaceutici srl).

Six days after the first estradiol dose, the animals are inoculated intravaginally with $10^7$ yeast cells in 0.1 ml of saline solution. The number of cells in the vaginal fluid is counted by culturing 10 µl samples (using calibrated plastic loop, Disponoic, PBI, Milan, Italy) taken from each animal, on Sabouraud agar plate containing chloramphenicol (50 µg/ml) as previously described (De Bernardis, et al. 1999. J Infect Dis. 179:201-8). The rat is considered infected when at least 1 CFU is detected in the vaginal lavage, i.e. a count of $>10^3$ CFU/ml. Other vaginal samples are also stained by periodic acid-Schiff-van Gieson method for microscopic examination.

The compounds are assayed for their capacity to accelerate yeast clearance from the rat vaginal cavity challenged by a virulent vaginopathic *Candida* strain. Relevant control conditions are adopted. Interpretation of the results is based on two main criteria: 1. the accelerated clearance during early treatment, i.e. three-six days from the intravaginal challenge; 2. the healing of infection (<1 CFU/µl of vaginal fluid) on day 21 post challenge. The differences are assessed by both parametrical (Student's t test) and non-parametrical (Manner Whitney U test) statistics. Two types of experiments are done (repeated three times), one of a preventative type and one of a therapeutic type. In the former experiments, a single compound administration is given intravaginally 30 min before intravaginal *Candida* challenge whereas in the latter the same compound is given at 1, 24 and 48 hrs after challenge. The experiment is conducted for each of the compounds (6a, 6b, etc.) and each provides an effective treatment against the vaginal yeast infection.

Example 5C

Systemic Control of *Candida* Infection

The ability of the compounds to control a systemic infection of *C. albicans* is assessed using standard methods. Briefly, mice are chronically infected with *C. albicans* by injecting $1 \times 10^6$ cells per mouse via the lateral tail vein (in 0.2 ml saline) and compounds are administered. Survival rates compared with control animals are measured and each of the compounds (6a, 6b, etc.) promotes survival.

The compounds can also be used to confer passive protection against yeast infection in vulnerable subjects by administering an effective dose prior to any possible infection. An effective dose can be determined by means known to those skilled in the art.

The experiments are repeated with infections caused by yeasts such as *tropicalis, glabtrata, krusei, norvegensis* or *inconspicua* and similarly effective results are obtained for each of the compounds.

As will be understood by one of ordinary skill in the art, each embodiment disclosed herein can comprise, consist essentially of or consist of its particular stated element, step, ingredient or component. As used herein, the transition term "comprise" or "comprises" means includes, but is not limited to, and allows for the inclusion of unspecified elements, steps, ingredients, or components, even in major amounts. The transitional phrase "consisting of excludes any element, step, ingredient or component not specified. The transition phrase" consisting essentially of limits the scope of the embodiment to the specified elements, steps, ingredients or components and to those that do not materially affect the embodiment. As used herein, a material effect would result in a statistically significant reduction in the effectiveness of a compound in treating cancer, a parasitic infection or a yeast infection.

Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques. When further clarity is required, the term "about" has the meaning reasonably ascribed to it by a person skilled in the art when used in conjunction with a stated numerical value or range, i.e. denoting somewhat more or somewhat less than the stated value or range, to within a range of ±20% of the stated value; ±19% of the stated value; ±18% of the stated value; ±17% of the stated value; ±16% of the stated value; ±15% of the stated value; ±14% of the stated value; ±13% of the stated value; ±12% of the stated value; ±11% of the stated value; ±10% of the stated value; ±9% of the stated value; ±8% of the stated value; ±7% of the stated value; ±6% of the stated value; ±5% of the stated value; ±4% of the stated value; ±3% of the stated value; ±2% of the stated value; or ±1% of the stated value.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements.

The terms "a," "an," "the" and similar referents used in the context of describing the invention (especially in the context of the following claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Certain embodiments of this invention are described herein, including the best mode known to the inventors for carrying out the invention. Of course, variations on these described embodiments will become apparent to those of ordinary skill in the art upon reading the foregoing description. The inventor expects skilled artisans to employ such variations as appropriate, and the inventors intend for the invention to be practiced otherwise than specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Furthermore, numerous references have been made to patents and printed publications throughout this specification. Each of the above-cited references and printed publications are individually incorporated herein by reference in their entirety.

In closing, it is to be understood that the embodiments of the invention disclosed herein are illustrative of the principles of the present invention. Other modifications that may be employed are within the scope of the invention. Thus, by way of example, but not of limitation, alternative configurations of the present invention may be utilized in accordance with the teachings herein. Accordingly, the present invention is not limited to that precisely as shown and described.

The particulars shown herein are by way of example and for purposes of illustrative discussion of the preferred embodiments of the present invention only and are presented in the cause of providing what is believed to be the most useful and readily understood description of the principles and conceptual aspects of various embodiments of the invention. In this regard, no attempt is made to show structural details of the invention in more detail than is necessary for the fundamental understanding of the invention, the description taken with the drawings and/or examples making apparent to those skilled in the art how the several forms of the invention may be embodied in practice.

Definitions and explanations used in the present disclosure are meant and intended to be controlling in any future construction unless clearly and unambiguously modified in the following examples or when application of the meaning renders any construction meaningless or essentially meaningless. In cases where the construction of the term would render it meaningless or essentially meaningless, the definition should be taken from Webster's Dictionary, 3rd Edition or a dictionary known to those of ordinary skill in the art, such as the Oxford Dictionary of Biochemistry and Molecular Biology (Ed. Anthony Smith, Oxford University Press, Oxford, 2004).

What is claimed is:

1. A compound having a structure

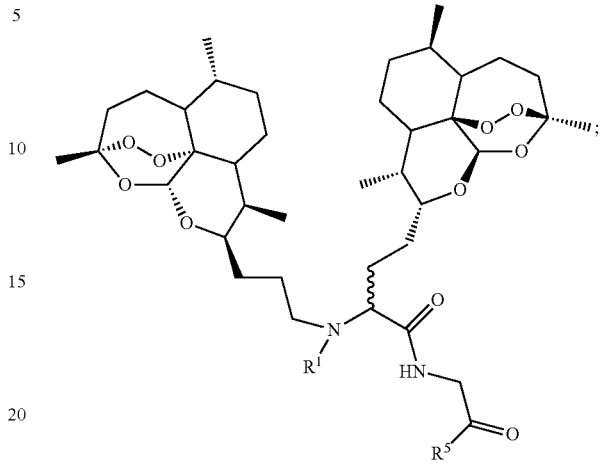

wherein $R^1$ is

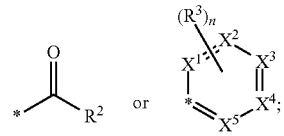

$R^2$ is H, $CH_3$, $CCl_3$, $CBr_3$, $CF_3$, OH, $NH_2$, or

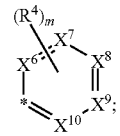

$R^3$ and $R^4$ are each independently H, Cl, Br, I, F, $CH_3$, $CCl_3$, $CBr_3$, $CF_3$, a $C_1$-$C_6$ alkyl substituted with one or more Cl, Br, OH, or F, $NO_2$, $CH_2OH$, $CH_2CH_2OH$, $OCH_3$, $OCH_2CH_3$, $CO_2H$, $NH_2$, $N(CH_3)_2$, $N(CCl_3)_2$, $N(CBr_3)_2$, or $N(CF_3)_2$;

$R^5$ is H, OH, $OCH_3$, or $OCH_2CH_3$;

n is 0, 1, 2, 3, 4, or 5;

m is 0, 1, 2, 3, 4, or 5; and $X^1$, $X^2$, $X^3$, $X^4$, $X^5$, $X^6$, $X^7$, $X^8$, $X^9$, and $X^{10}$ are each independently CH or N.

2. The compound of claim 1, wherein $X^1$, $X^2$, $X^3$, $X^4$, $X^5$, $X^6$, $X^7$, $X^8$, $X^9$, and $X^{10}$ are each independently CH or N.

3. The compound of claim 1, wherein $R^1$ is

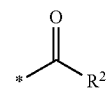

wherein $R^2$ is $CF_3$.

4. The compound of claim 1, wherein $R^3$ is $NH_2$ or $OCH_3$.

5. The compound of claim 1, wherein n is 1 and $R^4$ is $NO_2$.

6. The compound of claim 1, wherein n is 4 and $R^4$ is F.

7. The compound of claim 1, wherein $R^1$ is

and $R^2$ is

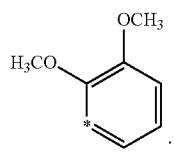

8. The compound of claim 1, wherein $R^5$ is OH.
9. The compound of claim 1, wherein $R^5$ is $OCH_3$.
10. The compound of claim 1 having a structure

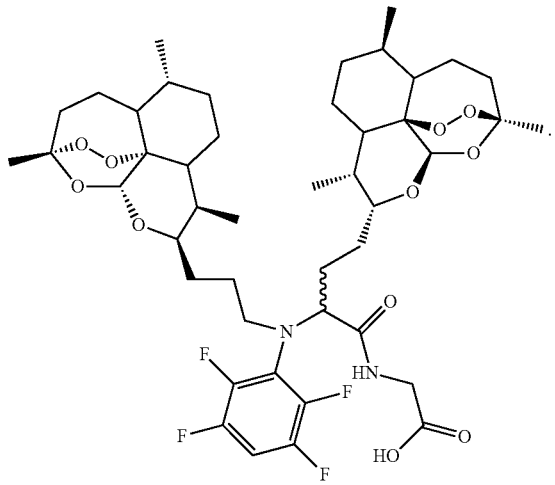

11. A compound having a structure

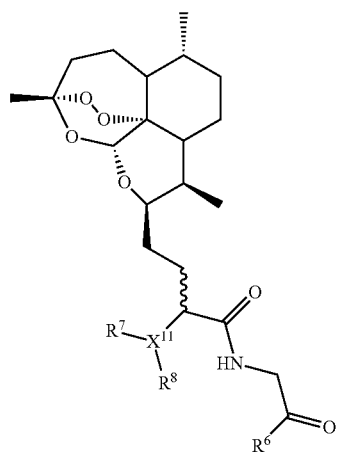

wherein $R^6$ is H, Cl, Br, I, F, $CH_3$, $CCl_3$, $CBr_3$, $CF_3$, a $C_1$-$C_6$ alkyl substituted with one or more Cl, Br, OH, or F, $NO_2$, OH, $CH_2OH$, $CH_2CH_2OH$, $OCH_3$, $OCH_2CH_3$, $CO_2H$, $NH_2$, $N(CH_3)_2$, $N(CCl_3)_2$, $N(CBr_3)_2$, or $N(CF_3)_2$;

$R^7$ is H, Cl, Br, I, F, $CH_3$, $CCl_3$, $CBr_3$, $CF_3$, a $C_1$-$C_6$ alkyl substituted with one or more Cl, Br, OH, or F, $CH(CH_3)_2$, $NO_2$, $CH_2OH$, $CH_2CH_2OH$, $OCH_3$, $OCH_2CH_3$, $CO_2H$, $NH_2$, $N(CH_3)_2$, $N(CCl_3)_2$, $N(CBr_3)_2$, or $N(CF_3)_2$;

$R^8$ is

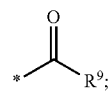

$R^9$ is H, $CH_3$, $CCl_3$, $CBr_3$, $CF_3$, OH, $NH_2$, or

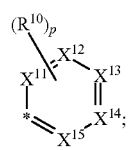

$R^{10}$ is H, Cl, Br, I, F, $CH_3$, $CCl_3$, $CBr_3$, $CF_3$, a $C_1$-$C_6$ alkyl substituted with one or more Cl, Br, OH, or F, $NO_2$, $CH_2OH$, $CH_2CH_2OH$, $OCH_3$, $OCH_2CH_3$, $CO_2H$, $NH_2$, $N(CH_3)_2$, $N(CCl_3)_2$, $N(CBr_3)_2$, or $N(CF_3)_2$;
p is 0, 1, 2, 3, 4, or 5; and
$X^{11}$, $X^{12}$, $X^{13}$, $X^{14}$, and $X^{15}$ are each independently CH or N.

12. The compound of claim 11, wherein $X^{11}$, $X^{12}$, $X^{13}$, $X^{14}$, and $X^{15}$ are each independently CH or N.
13. The compound of claim 11, wherein $R^9$ is

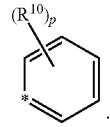

14. The compound of claim 11, wherein $R^7$ is $CH(CH_3)_2$.
15. The compound of claim 11, wherein $R^9$ is benzene.
16. The compound of claim 11, wherein p is 0.
17. The compound of claim 11, having a structure

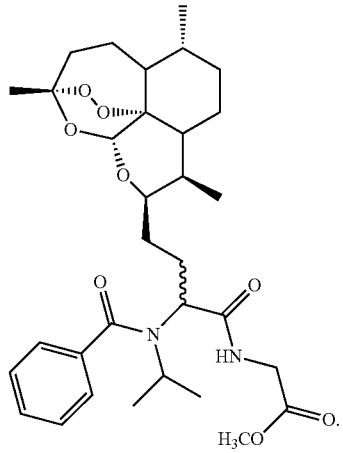

18. The compound of claim 1 conjugated to an iron-carrying molecule.

19. The compound of claim 18 wherein the iron-carrying molecules are transferrin, lactoferrin, iron chelators and iron nanoparticles.

20. A method of treating a condition comprising, administering a compound of claim 1 to a subject in need thereof, wherein the condition is a cancer, a parasitic infection or a yeast infection.

21. The method of claim 20 wherein the cancer is breast cancer, renal cancer, ovarian cancer, central nervous system cancer, colon cancer, lung cancer, leukemia, melanoma or prostate cancer.

22. The method of claim 20 wherein the parasitic infection is a malarial infection or a *coccidia* infection.

23. The method of claim 22 wherein the *coccidia* infection is a chicken *coccidia* infection.

* * * * *